United States Patent [19]
Allen et al.

[11] Patent Number: 5,374,560
[45] Date of Patent: Dec. 20, 1994

[54] METHOD FOR SCREENING AND DISTINGUISHING BETWEEN COBALAMIN AND FOLIC ACID DEFICIENCY BASED ON ASSAY FOR CYSTATHIONINE AND 2-METHYLCITRIC ACID

[75] Inventors: Robert H. Allen, Englewood; Sally P. Stabler, Denver, both of Colo.; John Lindenbaum, New York, N.Y.

[73] Assignee: The University of Colorado, Inc., Boulder, Colo.

[21] Appl. No.: 727,628

[22] Filed: Jul. 10, 1991

Related U.S. Application Data

[63] Continuation-in-part of Ser. No. 333,124, Apr. 3, 1989, abandoned, and a continuation-in-part of Ser. No. 345,885, May 1, 1989.

[51] Int. Cl.⁵ .................... G01N 33/50; G01N 33/68; G01N 30/04; G01N 1/34
[52] U.S. Cl. .................................. 436/129; 436/56; 436/89; 436/120; 436/161; 436/174; 436/177
[58] Field of Search .................... 436/56, 88, 89, 161, 436/173, 74, 76, 92, 129, 174, 175, 177, 120

[56] References Cited

U.S. PATENT DOCUMENTS 4,940,658 7/1990 Ellen et al. ............................ 436/86

OTHER PUBLICATIONS

Stabler et al., "Assay of Methylmalonic Acid in the Serum of Patients with Cobalamin Deficiency Using Capillary Gas Chromatography-Mass Spectrography", J. Clin. Invest., 77, May 1986 1606–1612.
Baretz et al., "Metabolism in Rats in Vivo of Isobutyrates Labeled with Stable Isotopes at Various Positions", The Journal of Bio. Chem., vol. 253 (12) Jun. 12, 4203–4213.
"Elevation of Total Hemocysteine in the Serum of Patiens with Cobalamin of Dolate Def. Detected by Capillary gas Chrom.—Mass Spect.", J. Clin Invest., vol. 81, Feb. 1988 446–74.
Ledley et al., "Benign Methylmalonic Acidinia", The New England of Medicine, vol. 311 (16), 1015–18.
Stabler et al., "Inhibition of Cobalamin-Dependent Enzymes by Cobalamin Analagues in Rats", J. Clin. Invest. vol. 87, Apr. 1991, 1422–30.
Stabler et al., "Failure to Detect β-Leucine in Human Blood or Leucine 2,3-Aminomutox in Rat Liver Using Capillary Gas Chrom.-Mass Spect.", J. Biol. Chem. vol. 263 (12), Apr. 25, 5581–5588, 1988.
J. David Rawn, Biochemistry, 1989, pp. 433, 476.
Stabler et al., J. Clin. Invest., Feb. 1988 pp. 466–474.
Sweetman et al., Stable Isotopes, 1982, pp. 287–293.
Stabler et al., J. Clin Invest, May 1986 pp. 1606–1612.
Norman et al, "Bloob" Jun. 1982, pp. 1128–1131.
Marcell et al, Analytical Chemistry, 1985, pp. 58–66.

*Primary Examiner*—James C. Housel
*Assistant Examiner*—Milton I. Cano
*Attorney, Agent, or Firm*—Beaton & Swanson

[57] ABSTRACT

A method for screening and distinguishing between cobalamin deficiency and folic acid deficiency by relating elevated levels of cystathionine to cobalamin or folic acid deficiency and relating elevated levels of 2-methylcitric acid to cobalamin deficiency but not folic acid deficiency. The methods can be used alone or in combination with other methods for detecting and distinguishing between cobalamin deficiency and folic acid deficiency.

69 Claims, 8 Drawing Sheets

2- Methylcitric Acid Derivative ($M^+ = 662$)

METHOD FOR SCREENING AND DISTINGUISHING BETWEEN COBALAMIN AND FOLIC ACID DEFICIENCY BASED ON ASSAY FOR CYSTATHIONINE AND 2-METHYLCITRIC ACID

RELATED APPLICATIONS

This application is a continuation-in-part of application Ser. No. 333,124 filed Apr. 3, 1989 now abandoned and application Ser. No. 345,885 filed May 1, 1989.

FIELD OF THE INVENTION

This invention relates to a method of diagnosing cobalamin deficiency and folic acid deficiency and distinguishing between the two, in warm-blooded animals, particularly humans, by measuring serum levels of cystathionine and 2-methylcitric acid.

BACKGROUND OF THE INVENTION

Accurate and early diagnosis of cobalamin (Vitamin $B_{12}$) and folic acid deficiencies in warm-blooded animals is important because these deficiencies can lead to life-threatening hematologic abnormalities which are completely reversible by treatment with cobalamin or folic acid, respectively. Accurate and early diagnosis of cobalamin deficiency is especially important because it can also lead to incapacitating and life-threatening neuropsychiatric abnormalities; administration of exogenous cobalamin stops the progression of these abnormalities, almost always leads to significant improvement in symptoms, and frequently leads to their complete correction. The distinction between cobalamin and folic acid deficiency is often difficult because both deficiencies lead to indistinguishable hematologic abnormalities; the distinction is important because use of the proper vitamin results in the greatest improvement in hematologic abnormalities and, more importantly, only cobalamin will correct the neuropsychiatric abnormalities which are only seen in cobalamin deficiencies. The use of folic acid to treat cobalamin deficiency is extremely dangerous, since some or all of the hematologic abnormalities may improve, but neuropsychiatric abnormalities will not improve and may progress, or even be precipitated.

Assays for cobalamin and folate in serum or plasma have long been the most widely utilized and recommended tests for diagnosing and distinguishing cobalamin and folic acid deficiency. However, in 1978 it was discovered that cobalamin analogues are present in human plasma and that their presence could mask cobalamin deficiency because the radioisotope dilution assays for serum cobalamin then in use were not specific for true cobalamin. This problem could be corrected by using pure or purified intrinsic factor as the binding protein in the radioisotope dilution assay for cobalamin. This modification has almost totally replaced assays existing in 1978 that used a nonspecific cobalamin-binding protein. See, e.g., U.S. Pat. No. 4,188,189 (Allen), U.S. Pat. No. 4,351,822 (Allen), U.S. Pat. No. 4,451,571 (Allen), and Kolhouse, J. F., H. Kondo, N. C. Allen, E. Podell, and R. H. Allen, *N. Eng. J. Med.* 299:785–792 (1978). These improved assays for serum cobalamin are now utilized in thousands of laboratories throughout the world and appear to give low values for about 90% of patients with cobalamin deficiency. R. H. Allen, S. P. Stabler, D. G. Savage and J. Lindenbaum, *American Journal of Hematology*, 34:90–98 (1990); J. Lindenbaum, D. G. Savage, S. P. Stabler and R. H. Allen, *American Journal of Hematology*, 34:99–107 (1990); S. P. Stabler, R. H. Allen, D. G. Savage and J. Lindenbaum, *Blood*, 76(5): 871–81 (1990).

The improved assays avoid the problem of cobalamin analogues masking true cobalamin deficiency, but they have been severely criticized because they frequently give low values in patients who lack any evidence of actual cobalamin deficiency. This problem of false positive testing led experts in the field to take the position that cobalamin deficiency should be considered and serum cobalamin values should be obtained only in patients who have hematologic or neurologic abnormalities that are typical of patients with cobalamin deficiency. Dr. Schilling and his coworkers, who are experts in the field of cobalamin deficiency and laboratory diagnosis, stated:

"We conclude that the 'improved' vitamin $B_{12}$ assay kits will yield an increased proportion of clinically unexplained low results for serum $B_{12}$.

It seems prudent for scientific and economic reasons to measure serum vitamin $B_{12}$ only in patients who have hematological or neurological findings that suggest a reasonable probability of vitamin $B_{12}$ deficiency. Measuring serum $B_{12}$ as a screening test in the anemic or the geriatric population will result in a high proportion of low values that cannot be correlated with clinical disease."

Schilling, R. F., V. F. Fairbanks, R. Miller, K. Schmitt, and M. J. Smith, *Clin. Chem.* 29(3):582–583 (1983).

Thus, the cobalamin assays referred to by Dr. Schilling frequently provided low serum cobalamin levels in patients who were not truly cobalamin deficient. Such findings are confusing or misleading to the physician and may result in unnecessary and expensive further testing. To avoid that, it was generally taught in the art that the clinical spectrum of cobalamin deficiency is relatively narrow and well-defined and that the possibility of cobalamin deficiency should only be considered in those who have concurrent hematological or neurological symptoms. Routine screening of the general population or those with only moderate anemia, or moderate macrocytosis, or other neuropsychiatric abnormalities, would lead to high numbers of false positives.

It was thought that the hematological or neurological symptoms that were necessary to justify an assay for serum cobalamin and the resulting risk of a false positive, were fairly severe. Those symptoms included significant anemia, displayed for example in decreased hematocrit or hemoglobin, with macrocytic red blood cells (i.e., mean cell volume (MCV) generally greater than 100 fl), or neurologic symptoms of peripheral neuropathy and/or ataxia. Anemia associated with cobalamin deficiency was described as typically severe with hemoglobin $\leq 8$ g % or hematocrit $<25\%$ and the size of the red blood cells was described as greatly increased to levels $>110$ fl. See, for example, Babior and Bunn (1983) in *Harrison's Principles of Internal Medicine* (Petersdorf et al., eds.) McGraw-Hill Book Co., New York; Lee and Gardner (1984) in *Textbook of Family Practice*, 3rd Ed. (Rakel, ed.) Saunders & Co, Philadelphia). While it was well recognized that individuals with cobalamin deficiency could display neurologic disorders in the absence of anemia, such situations were believed to be exceptional and rare. See Beck (1985) in *Cecil Textbook of Medicine*, 17th Ed. (Wyngaarden and Smith, eds.) W. B. Saunders, Philadelphia, p. 893-900; Babior and Bunn (1987) in Harrison's *Principles of Internal Medicine*, 11*th Ed.* (Braunwald et al., eds.) McGraw-Hill, New York pp. 1498-1504; Walton (1985) *Brain's Diseases of the Nervous System, 9th Ed.* Oxford University Press, Oxford, UK. The neurologic symptoms of cobalamin deficiency were considered to be late manifestations of the disease most typically occurring after the onset of anemia or, if they occurred first, were soon to be followed by the onset of anemia. See Woltmann (1919) *Am. J. Med. Sci.* 157:400-409; Victor and Lear (1956) *Am. J. Med.* 20:896-911.

It was later discovered that the clinical spectrum of cobalamin deficiency is much broader than previously recognized and that many cobalamin-deficient patients are not anemic, or only moderately anemic; that in many cases their red blood cells are not macrocytic, or only moderately macrocytic; that in many cases a variety of neurologic abnormalities other than peripheral neuropathy and ataxia are present; and that in many cases the serum cobalamin level is only slightly decreased and may actually be normal, even with the improved assays using purified intrinsic factor. See U.S. Pat. No. 4,940,658 by Allen et al; S. P. Stabler, R. H. Allen, D. G. Savage and J. Lindenbaum, *Blood*, 76(5): 871-81 (1990). Accordingly, there was a need for an improved assay for cobalamin deficiency, preferably one in which cobalamin deficiency could be distinguished from folic acid deficiency.

An improved assay is disclosed in U.S. Pat. No. 4,940,658, the contents of which are hereby incorporated by reference, by Allen et al., who are the inventors of the present invention. The Allen et al. patent teaches a method of assaying total homocysteine serum concentrations to predict cobalamin or folic acid deficiency, and assaying serum methylmalonic acid concentrations to distinguish between the two deficiencies. Briefly, it was determined that there were elevated levels of total homocysteine in about 85-95% of patients with cobalamin deficiency and in about 90-95% of patients with folic acid deficiency. Therefore, elevated homocysteine levels pointed toward one of those two deficiencies, but did not distinguish between the two. However, distinguishing between the two was assisted by the discovery that there were elevated levels of methylmalonic acid in about 85-95% of patients with cobalamin deficiency but methylmalonic acid levels were normal in patients with folic acid deficiency. The two assays are relatively inexpensive and accurate, and can be performed concurrently by taking a single serum sample.

The assay described in the Allen patent is a very important test procedure but may not be infallible in detecting either kind of deficiency or in distinguishing between the two. About 5-15% of the cobalamin deficiencies will not be detected because these patients will not show elevated homocysteine levels. About 5-10% of the folic acid deficiencies will not be detected because these patients will not show elevated homocysteine levels. When elevated homocysteine. Levels are in fact detected, thereby indicating either a cobalamin deficiency or folic acid deficiency, about 5-10% of the cobalamin deficiencies can not be distinguished from the folic acid deficiencies because the patients will not show elevated methylmalonic acid levels. Therefore the assays may produce a small but not insignificant number of false negative results.

The existence of this small potential of false negative results led the inventors of the present invention to develop another assay procedure to detect cobalamin and folic acid deficiencies and to distinguish between the two. It has been discovered that elevated levels of cystathionine are present in the serum and urine of about 80-90% of patients with cobalamin deficiency or folic acid deficiency. It has also been discovered that elevated levels of 2-methylcitric acid are present in the serum, urine and cerebral spinal fluid of 80-90% of patients with cobalamin deficiency but not in patients with folic acid deficiency. The present invention uses an assay for cystathionine as a test for the existence of either of the two deficiencies or as a check on an assay for total homocysteine when testing for the two deficiencies. It also uses an assay for 2-methylcitric acid as a test for distinguishing between the two deficiencies or as a check on an assay for methylmalonic acid in distinguishing between the two deficiencies.

It was previously known that increased amounts of cystathionine are present in the urine and serum of children and adults with inherited defects of cystathionase who cannot convert cystathionine to cysteine and alpha-ketobutyrate. The serum levels of cystathionine range from undetectable to as high as 80,000 nanomoles per liter. Serum levels of methionine, homocysteine and cysteine are usually not elevated in these patients. See, e.g., Mudd, S. H., H. L. Levy and F. Skovby, in *The Metabolic Basis of Inherited Disease*, 6th Ed. (C. R. Scriver, A. L. Beaudet, W. S. Sly and D. Valle, eds.) (McGraw-Hill, Inc., New York, 1989) pp. 693-734. Elevated levels of urine cystathionine have also been seen in a variety of other conditions including pyridoxine (Vitamin $B_6$) deficiency, hyperthyroidism, liver disease, various tumors of the central nervous system and liver, and inherited defects of cystathionine transport in the kidney. See, e.g., Mudd, S. H., in *The Metabolic Basis of Inherited Disease*, supra.

Elevated levels of cystathionine are present in the urine and serum of some children with inherited defects involving methionine synthase, who cannot convert homocysteine and $N^5$-methyltetrahydrofolate to methionine and tetrahydrofolate, respectively. These patients usually have low levels of methionine, high levels of total homocysteine, and normal levels of cysteine in their serum. In these patients, the inherited defects were due to: 1) failure to synthesize $N^5$-methyltetrahydrofolate; 2) failure to synthesize methylcobalamin, which is a required co-factor for methionine synthase; and 3) a lack of the plasma transport protein transcobalamin II, which is required to deliver cobalamin to cells. See, e.g., Levy, H. L., S. H. Mudd, J. D. Schulman, P. M. Dryfus, and R. H. Abeles, *Am. J. Med.* 48:390-397, 197; Baumgartner, E. R., H. Wick, R. Mauere, N. Egli, and B. Steinmann, *Helv. Paediat. Acta* 34:.465-482, 1979; Ribes, A., M. A. Vilaseca, P. Briones, A. Maya; J. Sabater, P. Pascual, L. Alvarez, J. Ros and E. G. Pascual, *J. Inher. Metabol. Dis.* 7(Suppl. 2):129-130, 1984; Baumgartner, R., H. Wick, J. C. Linnell, E. Gaull, C. Bachmann, and B. Steinmann, *Helv. Paediat. Acta.* 34:483-496, 1979; Mudd, S. H., in *The Metabolic Basis of Inherited Disease*, supra; Carmel, R., A. A. Bedros, J. W. Mace, and S. I. Goodman, *Blood* 55:570-579, 1980.

On the other hand, other children with similar defects did not have elevated levels of cystathionine, which tended to cast doubt on the reliability of such an indicator. See, e.g., Goodman, S. I., P. G. Moe, K. B. Hammond, S. H. Mudd, and B. W. Uhlendorf, *Biochem. Med*

4:500–515, 1970; Barshop, B. A., J. Wolff, W. L. Nyhan, A. Yu, C. Pordanos, G. Jones, L. Sweetman, J. Leslie, J. Holm, R. Green, D. W. Jacobsen, B. A. Cooper, and D. Rosenblatt, *Am. J. Med. Genet.* 35:222–228, 1990; Baumgartner, R., H. Wick, H. C. Linnell, E Gaull, C. Bachmann, and B. Steinmann, *Helv. Paediat. Acta.* 34:483–496, 1979; Mudd, S. H., in *The Metabolic Basis of Inherited Disease*, supra.

Elevated levels of cystathionine have been reported in the serum of pigs with severe experimental vitamin $B_{12}$ deficiency. See Levy, H. L. and G. J. Cardinale, *Fed. Proc.* 29:634, 1970: Mudd, S. H., in *Heritable Disorders of Amino Acid Metabolism: Patterns of Clinical Expression and Genetic Variation*, (W. O. Nyhan, ed.) John Wiley & Sons, New York, 1974, pp. 429–451. Increased amounts of cystathionine have been observed in the urine of several children with life-threatening cobalamin deficiency. See Higgenbottom, M. C., L. Sweetman, and W. L. Nyhan, *N. Engl. J. Med.* 299:317–323, 1978; Davis, Jr., J. R., J. Goldenring, and B. H. Lugin, *Am. J. Dis. Child.* 135:566–567, 1981. In other infants with life-threatening cobalamin deficiency, amino acids in urine were found to be normal or cystathionine was present in undetectable or normal amounts. See Grasbeck, R., R. Gordin, I. Kantero, and B. Kuhlback, *Acta Medica Scandinavica.* 167:289–296, 1960; Lambert, H. P., T. A. J. Prankerd, and J. M. Smellie, *Q. J. Med.* 30:71–92, 1961; Lampkin, B. C. and A. M. Mauer, *Blood* 30:495–502, 1967; Hollowell, Jr., J. G., W. K. Hall, M. E. Coryell, J. McPherson, Jr., and D. A. Hahn, *Lancet* 2:1428, 1969; Frader, J., B. Reibman, and D. Turkewitz, *N. Engl. J. Med.* 299:1319–1320, 1978. Cystathionine was not detected in the serum or urine of a child with life-threatening folic acid deficiency although it may have been present in this patient's cerebral spinal fluid. See Corbeel, L., G. Van den Berghe, J. Jaeken, J. Van Tornout, and R. Eeckels, *Eur. J. Pediatr.* 143:284–290, 1985. It is believed that elevated cystathionine has not been reported in the serum or urine of children with moderate or mild cobalamin or folic acid deficiencies, or in adults with any degree of cobalamin or folic acid deficiencies, or in the serum of normal children or adults.

It was previously known that large amounts of 2-methylcitric acid are present in the urine of children with inherited defects in propionyl-CoA carboxylase, who cannot convert propionyl-CoA to D-methylmalonyl-CoA, and with inherited defects in L-methylmalonyl-CoA mutase, who cannot convert L-methylmalonyl-CoA to succinyl-CoA. See, e.g., Ando, T., K. Rasmussen, J. M. Wright, and W. L. Nyhan, *J. Biol. Chem.* 247:2200–2204, 1972: Sweetman, L., W. Weyler, T. Shafai, P. E. Young, and W. L. Nyhan, *JAMA* 242:1048–1052, 1979; Weidman, S. W. and G. R. Drysdale, *Biochem. J.* 177:169–174, 1979. It has also been reported that 2-methylcitric acid is present in increased amounts in the amniotic fluid and urine of pregnant women with fetuses that were shown after birth to have inherited defects in either propionyl-CoA carboxylase or L-methylmalonyl-CoA mutase. See Naylor, G., L. Sweetman, W. L. Nyhan, C. Hornbeck, J. Griffiths, L. Morch, and S. Brandange, *Clinica Chimica Acta* 107:175–183, 1980; Sweetman, L., G. Naylor, T. Ladner, J. Holm, W. L. Nyhan, C. Hornbeck, J. Griffiths, L. Morch, S. Brandange, L. Gruenke, and J. C. Craig, in *Stable Isotopes* (H. L. Schmidt, H. Forstel, and K. Heinzinger, eds.) Elsevier Scientific Publishing Company, Amsterdam, 1982, pp. 287–293; Aramaki, S., D. Lehotay, W. L. Nyahn, P.M. MacLeod and L. Sweetman, *J. Inher. Metab. Dis.* 12:86–88, 1989; Coude, M., B. Chadefaux, D. Rabier, and P. Kamound, *Clinica Chimica Acta.* 187:329–332, 1990.

Elevated levels of 2-methylcitric acid have also been observed in the urine of some (Barshop, B. A., J. Wolff, W. L. Nyhan, A. Yu, C. Prodanos, G. Jones, L. Sweetman, J. Leslie, J. Holm, R. Green, D. W. Jacobsen, B. A. Cooper, and D. Rosenblatt, *Am. J. Med. Genet.* 35:222–228, 1990; Baumgartner, R., H. Wick, J. C. Linnell, E. Gaull, C.Bachmann, B. Steimann, *Helv. Paediat. Acta.* 34:483–496, 1979; Higgenbottom, M. C., L. Sweetman, and W. L. Nyhan, *N. England J. Med.* 299:317–323, 1978) but not all (Levy, H. L., S. H. Mudd, J. D. Schulman, P. M. Dreyfus, and R. H. Abelese, *Am. J. Med.* 48:390–397, 1970; Baumgartner, E. R. H. Wick, R. Maurer, N. Egli, and B. Steinmann, *Helv. Paediat. Acta.* 34:465–482, 1979; Ribes, A., M. A. Vilaseca, P. Briones, A. Maya and J. Sabater, J. Inherit. Metabol. Dis. 7(Suppl. 2):129–130, 1984; Mudd, S. H., and B. W. Uhlendorf, *Biochem. Med.* 4:500-515, 1970; Carmel, R., A. A. Bedros, J. W. Mace, and S. I. Goodman, *Blood* 55:570–579, 1980) children with inherited defects involving: 1) the inability to convert cobalamin to adenosyl-cobalamin, which is a required co-factor for L-methylmalonyl-CoA mutase; and 2) transcobalamin II deficiency which results in the inability to transport cobalamin from plasma to cells.

Large amounts of 2-methylcitric acid have been found in the urine of one child with life-threatening cobalamin deficiency. See Higgenbottom, M. C. L. Sweetman, and W. L. Nyhan, *N. Engl. J. Med.* 299:317–323, 1978. In other infants with life-threatening cobalamin deficiency, the presence or elevated levels of 2-methylcitric acid were not observed. See Davis, Jr., J. R., J. Goldenring, and B. H. Lubin, *Am. J. Dis. Child.* 135:566–567, 1989; Hollowell, Jr. J. G., W. K. Hall, M. E. Coryell, J. McPherson, Jr., and D. A. Hahn, *Lancet* 2:1428, 1969; Frader, J., Reibman, and D. Turkewitz, *N. Engl. J. Med.* 299:1319–1320, 1978). It is believed that the presence of 2-methylcitric acid in detectable or elevated amounts has not been reported in the urine of children with moderate or mild cobalamin deficiency or adults with severe, moderate or mild cobalamin deficiency. The presence of 2-methylcitric acid in detectable or elevated amounts has not been reported in the serum of any subject with any of the inherited disorders involving propionyl-CoA carboxylase, L-methylmalonyl-CoA mutase, the synthesis of adenosyl cobalamin or the plasma transport of cobalamin nor has it been reported in the serum of children or adults with any degree of cobalamin deficiency nor in the serum of normal children or adults.

SUMMARY OF THE INVENTION

The present invention measures cystathionine levels in the serum or urine and measures 2-methylcitric acid levels in the serum, urine or cerebral spinal fluid for the purpose of predicting cobalamin and folic acid deficiencies and for distinguishing between the two deficiencies. It has been determined that elevated cystathionine levels tend to correspond with the existence of either such deficiency, while elevated 2-methylcitric acid levels tend to correspond with the existence of cobalamin deficiency but not folic acid deficiency and can thereby be used to distinguish between the two deficiencies.

In a preferred embodiment, samples of serum or urine in the assay for cystathionine, and samples of serum, urine or cerebral spinal fluid in the assay for 2-methylcitric acid, are mixed by vortexing with water and known amounts of stable isotope forms of cystathionine or 2-methylcitric acid, respectively. The mixtures are washed, incubated, eluted and dried in the manner described herein, and then are analyzed by gas chromatography/mass spectrometry.

The assays for cystathionine and 2-methylcitric acid may be combined with assays for homocysteine or methylmalonic acid or both. Further, while the assays are described for use with serum or urine in the case of cystathionine and with serum, urine or cerebral spinal fluid in the case of 2-methylcitric acid, it should be appreciated that "serum" may include plasma and that it may be feasible to apply the assays to other body fluids as well.

DETAILED DESCRIPTION OF THE INVENTION

The Metabolism

Figure 1:
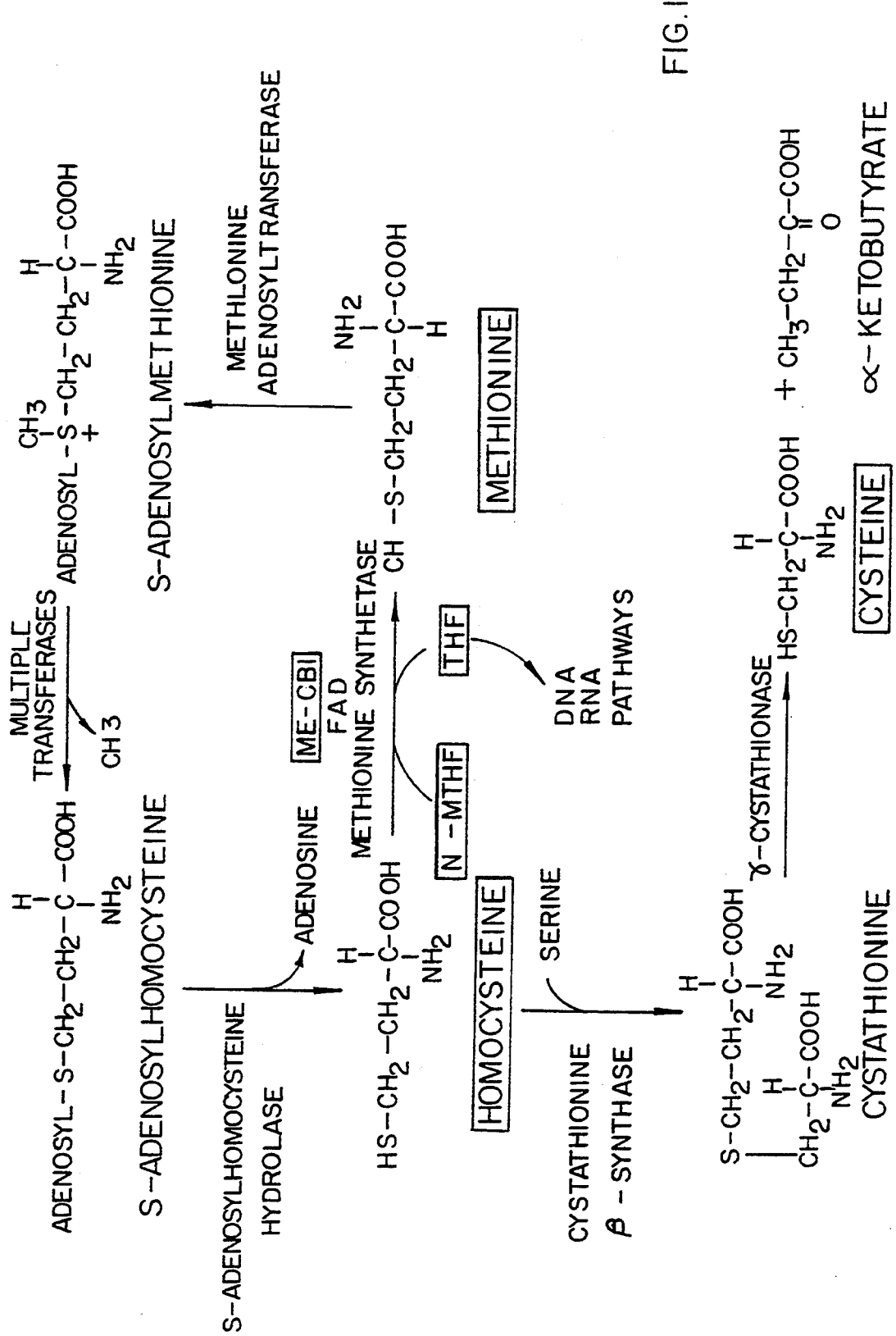
FIG. 1 shows a diagram of the metabolic pathways of homocysteine, methionine and cystathionine in humans.

The metabolism of homocysteine, methionine and cystathionine in humans is generally known and is shown diagrammatically in FIG. 1. Methionine is converted to S-adenosylmethionine by the transfer of the adenosyl moiety of ATP to methionine. S-adenosylmethionine is a high energy compound, and each sulfonium atom is capable of participating in one or more transfer reactions to produce the sulfur-containing compound S-adenosylhomocysteine. Hydrolysis cleaves S-adenosylhomocysteine into homocysteine and adenosine.

Homocysteine may be converted to cystathionine by the transsulfuration pathway or may be remethylated to form methionine. In methylation, the reaction utilizes $N^5$-methyltetrahydrofolate ($N^5$-MTHF) as the methyl donor and utilizes methylcobalamin as a cofactor. The remethylation of homocysteine results in methionine and tetrahydrofolate, the later of which is converted back to $N^5$-MTHF by DNA and RNA pathways. A deficiency in either folic acid or cobalamin will block the methylation of homocysteine into methionine. Such a block may lead to increases in serum or urine levels of homocysteine and cystathionine, although this outcome is not necessarily apparent in view of the complexity of the metabolic pathways and the possibility of other reactions.

In the synthesis of cystathionine from homocysteine in the transsulfuration pathway, the homocysteine is condensed with serine in a reaction catalyzed by cystathionine β synthase. Cystathionine cleaves into cysteine and α-ketobutyrate in a reaction catalyzed by γ-cystathionase to complete the transsulfuration sequence.

Figure 4:
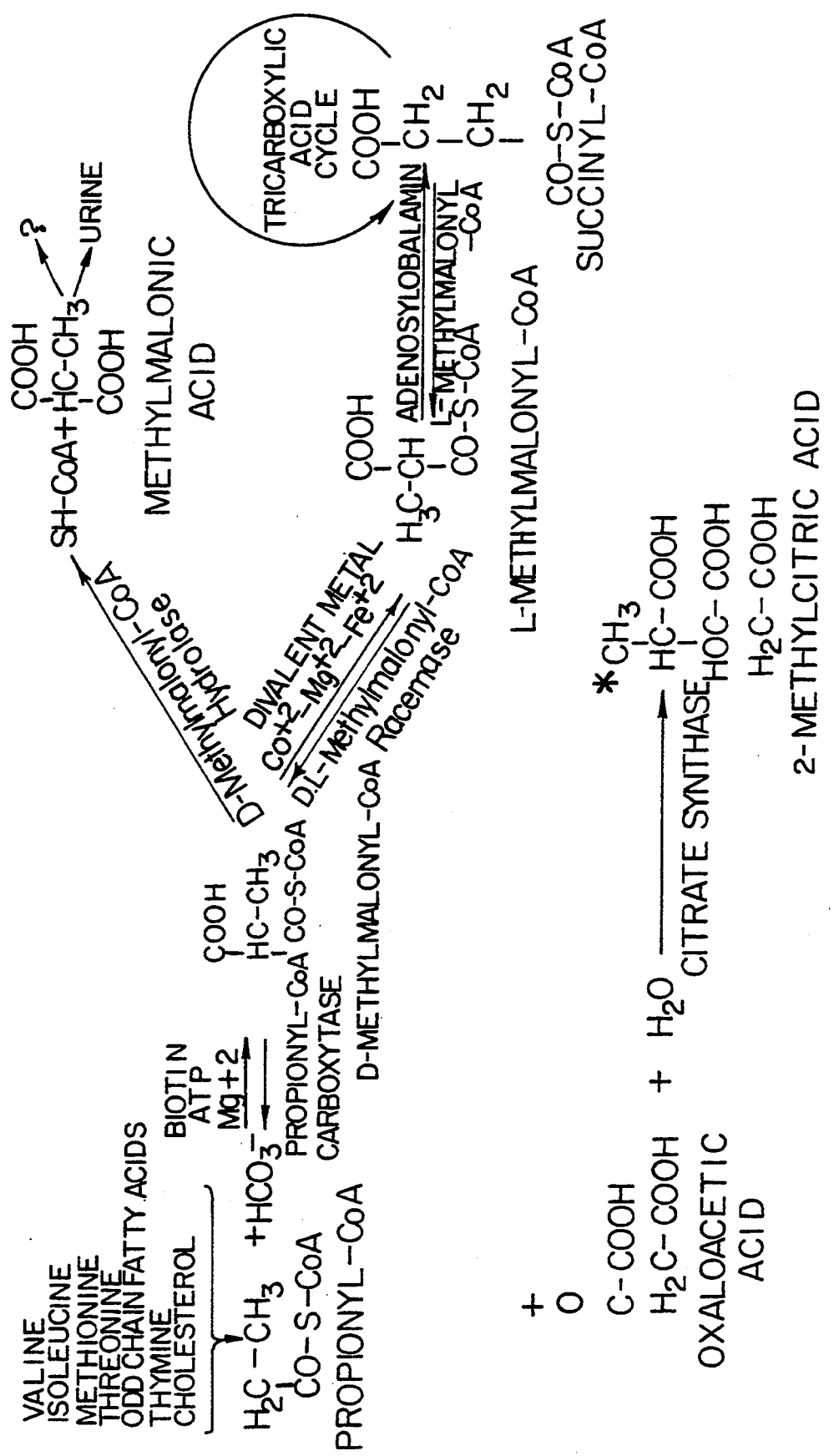
FIG. 4 shows a diagram of the metabolic pathways of 2-methylcitric acid and methylmalonic acid.

In the pathway for the formation of methylmalonic acid, shown in FIG. 4, propionyl-CoA is converted Into methylmalonyl-CoA. The methylmalonyl is converted to succinyl-CoA in a reaction requiring adenosylcobalamin as a cofactor. A deficiency in cobalamin may block the conversion of methylmalonyl-CoA to succinyl-CoA, thereby resulting in methylmalonic aciduria or propionic aciduria, although again such an outcome is not necessarily apparent from the metabolic pathway because a variety of other reactions could occur.

In the synthesis of 2-methylcitric acid, propionyl-CoA and oxaloacetic acid and water react to form 2-methylcitric acid, using the enzyme citrate synthase as a catalyst. It has been found that the blocking of the pathway from propionyl-CoA to succinyl-CoA by a deficiency of adenosylcobalamin may increase the conversion of propionyl-CoA to 2-methylcitric acid, thereby increasing 2-methylcitric acid levels.

Thus it can be seen that cobalamin (in the form of methylcobalamin) and folic acid are vital to the methylation of homocysteine into methionine, and that cobalamin (in the form of adenosylcobalamin) but not folic acid is vital to the conversion of methylmalonyl-CoA to succinyl-CoA. A deficiency in either cobalamin or folic acid may lead to increased levels of homocysteine or cystathionine. A deficiency in cobalamin but not folic acid may also result in increased levels of methylmalonic acid or 2-methylcitric acid.

Assay for Cystathionine

A preferred embodiment of the invention utilizes an assay for cystathionine levels in the manner described below. The following components are added in sequence to 12×75 mm glass test tubes:

(1) 51 ul of $H_2O$ containing 40 picomoles of D, L [2,2,3,3-$D_4$] cystathionine, available from MSD Isotopes, Montreal, Canada, as a custom synthesis;

(2) 40 ul of serum or urine; and (3) 100 ul of $H_2O$.

The samples are mixed well by vortexing and 51 ul of 0.083 $H_3BO_3$-NaOH, pH 10.0, containing 16.6 mg/ml of D, L-dithiothreitol is followed by mixing. After incubation of iodacctamide is added followed by mixing. After incubating for 30 minutes at 40° C., 1 ml of 0.03N HCl is added followed by mixing and the samples are then applied to 300 ul columns of a cation exchange resin (AG MP-50, 100–200 mesh, hydrogen form (Bio-Rad Laboratories, Richmond, Calif.)) that has previously been washed with 1 ml of MeOH and 3.3 ml of $H_2O$, to remove any negatively charged salts. After the sample is applied, each column is washed twice with 3 ml of $H_2O$ and once with 3 ml of MeOH. Each column is then eluted with 1.1 ml of 4N $NH_4OH$ in MeOH. The eluates are taken to dryness by vacuum centrifugation in a Savant vacuum centrifuge. The dried eluates are then derivatized by adding 30 ul of a solution containing 10 ul of N-methyl-N(tert-butyl dimethylsylyl) trifluoracetamide and 20 ul of acetonitrile. After incubation at 40° C. for 60 minutes in sealed autosampler vials, 1 ul is analyzed by gas chromatography/mass spectrometry using a 10 meter SPB-1 capillary column (Supelco, Inc., Bellefonte, Pa.) that has an internal diameter of 0.25 mm and a 0.25 um film thickness.

Gas chromatography/mass spectrometry is performed using a Hewlett Packard 5890 Gas Chromatograph and a Hewlett Packard 5970 or 5971A Mass Selective Detector. The initial column temperature is 140° C. which is held for approximately 0.6 minutes after sample injection and is then increased to 300° C. at a rate of 30° C./minute. The mass selective detector is operated in the selected ion monitoring mode in which ions 362.2 are monitored for endogenous cystathionine and 366.2 for D,L[2,2,3,3-$D_4$] cystathionine. Cystathionine is quantitated by dividing the integrated area of the M/Z 362.2 peak that elutes at approximately 5.7 minutes (the exact times are determined daily with controls) by the integrated area of the M/Z 366.2 peak that elutes at the same time and then multiplying by 1,000 nanomoles/liter, which is the equivalent amount of D,L[2,2,3,3-$D_4$] cystathionine that was added to each sample.

In some experiments, the method may be altered in the following manner: 1) 51 ul of $H_2O$ containing 400 picomoles of D,L[2,2,3,3-$D_4$] cystathionine, 400 ul of serum (or 40 ul of urine with 360 ul of 0.15M NaCl), and 1 ml of $H_2O$ are added in the initial sequence; 2) 51 ul of 1N NaOH containing 10 mg/ml of dithiothreitol are added in place of the $H_3BO_3$ dithiothreitol prior to the first 30 minute incubation; 3) the addition of iodoacctamide and the second 30 minute incubation are omitted; 4) the 0.03N HCl is omitted and the samples are applied to 300 ul columns of an anion exchange resin (AG MP-1, 100–200 mesh, chloride form); and 5) samples are eluted with 0.04N acetic acid in methanol. Comparable results are obtained with both methods.

The same processes may be used to assay for total homocysteine if a suitable internal standard for added to the samples.

Figure 2A:
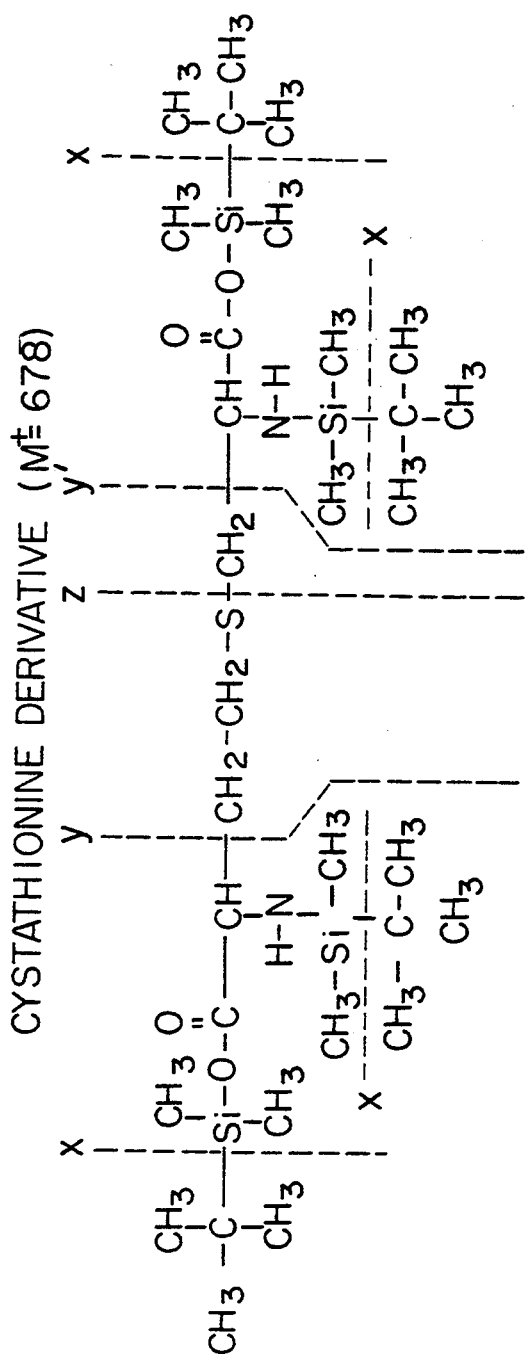
FIG. 2A and 2B illustrate the mass spectra of cystathionine.
Figure 2B:
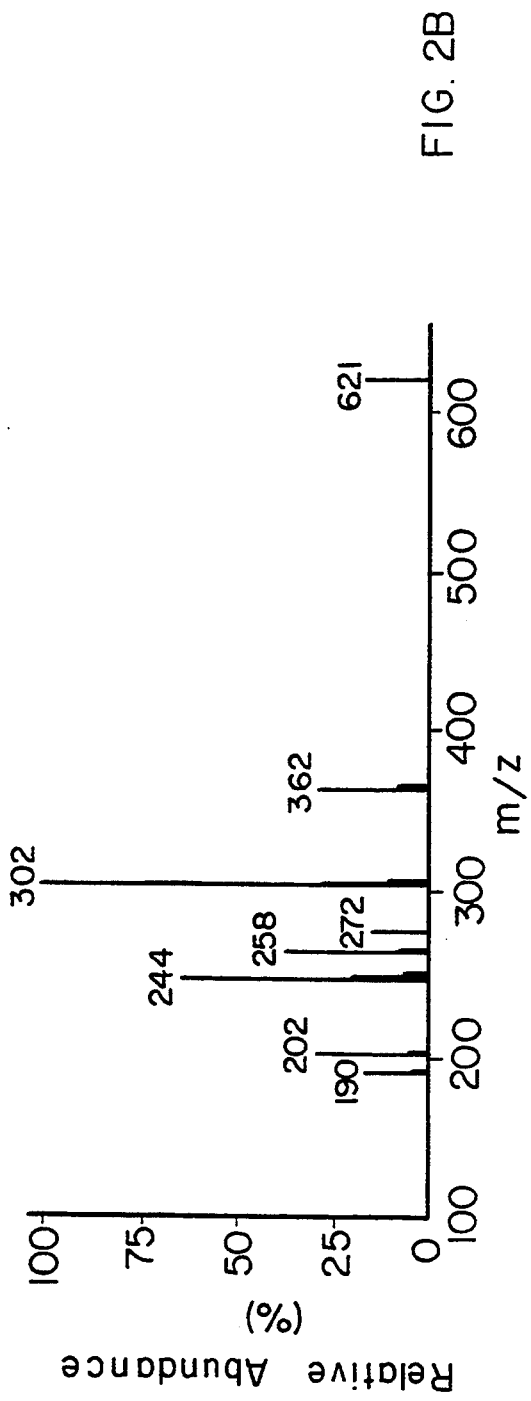
Figure 3A:
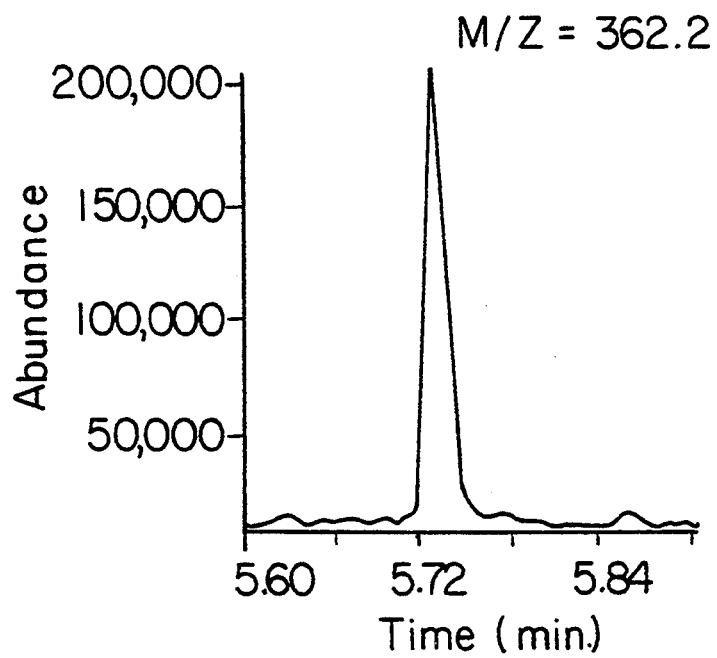
FIG. 3A and 3B illustrates the chromatograms of cystathionine.
Figure 3B:
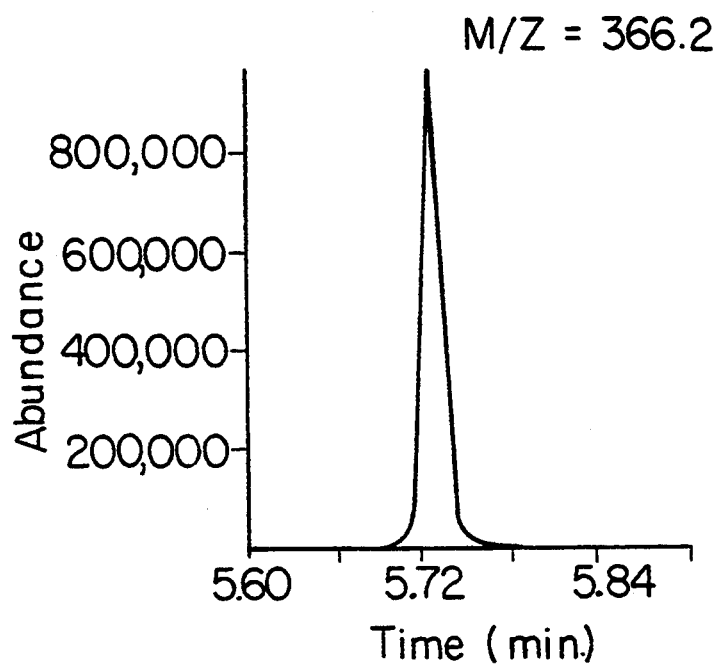

FIG. 2A and 2B show the molecular weights of cystathionine and a diagram of the cystathionine molecule. Peaks representing the entire derivative, i.e. $[M]^+$, were not observed. FIG. 3A and 3B shows the gas chromotogram of cystathionine, the top graph being for endogenous cystathionine and the bottom graph being for D,L[2,2,3,3-$D_4$] cystathionine.

Assay for 2-Methylcitric Acid

A preferred embodiment of the invention utilizes an assay for 2-methylcitric acid levels in the manner described below. The following components are each added in sequence to 12×75 mm glass test tubes:

1) 51 ul of $H_2O$ containing 200.4 picomoles of [methyl-$D_3$]2-methylcitric acid II and 172.8 picomoles of [methyl-$D_3$]2-methylcitric acid I available from MSD Isotopes, Montreal, Canada, as a custom synthesis;
2) 400 ul of serum, cerebral spinal fluid, or urine (in the case of urine, 40 ul are used together with 360 ul of 0.15M NaCl); and
3) 1 ml of $H_2O$.

The samples are mixed by vortexing and then applied to 300 ul columns of an anion exchange resin (AG MP-1, 100–200 mesh, chloride form (Bio-Rad Laboratories, Richmond, Calif.) that has previously been washed with 1 ml of MeOH and 3.3 ml of $H_2O$. After the sample is applied, each column is washed with 3 ml of $H_2O$ and 3 times with 3 ml of 0.01N acidic acid in MeOH. Each column is then eluted with 1.1 ml of 3.6M acidic acid/0.1N HCl in MeOH. The eluates are taken to dryness by vacuum centrifugation in a Savant vacuum centrifuge. The dried eluates are then derivatized by adding 30 ul of a solution containing 10 ul of N-methyl-N(tert-butyl dimethylsylyl)trifluoracetamide and 20 ul of acetonitrile. After incubation at 90° C. for 30 minutes in sealed autosampler vials, 1 ul is analyzed by gas chromatography/mass spectrometry using a 20 meter SPB-1 capillary column (Supelco, Inc.) that has an internal diameter of 0.25 mm and a 0.25 um film thickness.

Gas chromatography/mass spectrometry is performed using a Hewlett Packard 5890 Gas Chromatograph and a Hewlett Packard 5971A Mass Selective Detector. The initial column temperature is 80° C. which is held for approximately 0.6 minutes after sample injection and is then increased to 300° C. at a rate of 30° C./minute. The mass selective detector is operated in the selected ion monitoring mode in which ions 605.4 are monitored for endogenous 2-methylcitric acid II and I and 608.4 are monitored for [methyl-$D_3$]2-methylcitric acid II and I. 2-methylcitric acid II is quantitated by dividing the integrated area of the M/Z 605.4 peak that elutes at approximately 8.4 minutes (the exact times are determined daily with controls) by the integrated area of the M/Z 608.4 peak that elutes at the same time and then multiplying by 501 nanomoles/liter, which is the equivalent amount of [methyl-$D_3$]2-methylcitric acid II that was added to each sample. 2-methylcitric acid I is quantitated in the same manner utilizing the M/Z 605.4 and M/Z 608.4 peaks that elute at approximately minutes and then multiplying their ratio by 432 nanomoles/liter which is the equivalent amount of [methyl-$D_3$]2-methylcitric acid I added to each sample. The integrated areas for the two internal standard peaks, i.e. the M/Z 608.4 peaks eluting at about 8.4 and 8.5 minutes, are corrected for the amounts contributed to them by endogenous 2-methylcitric acid II and I, as a result of naturally occurring isotope abundance. These corrections, which are determined using samples containing only unenriched 2-methylcitric acid II and I, are approximately 6.6% of the areas of the 605.4 peaks at 8.4 and 8.5 minutes. It has been found that some serum, urine and cerebral spinal fluid samples contain an endogenous peak of M/Z 608.4 that elutes at the same time, i.e. approximately 8.5 minutes, as the M/Z 608.4 peak for 2-methylcitric acid I and that this endogenous peak interferes with the quantitation of endogenous 2-methylcitric acid in these samples. This problem can be solved by using the M/Z 608.4 peak for 2-methylcitric acid II as the internal standard for quantitation of 2-methylcitric acid I and 2-methylcitric acid II.

The same process may be used to assay for methylmalonic acid if a suitable internal standard for it is added to the samples.

Figure 5A:
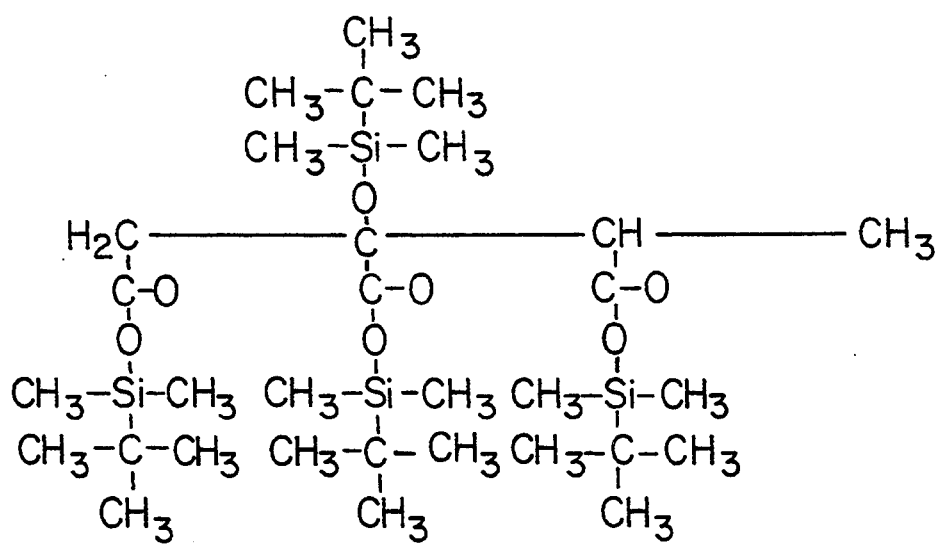
FIG. 5A and 5B illustrates the mass spectra of 2-methylcitric acid.
Figure 5B:
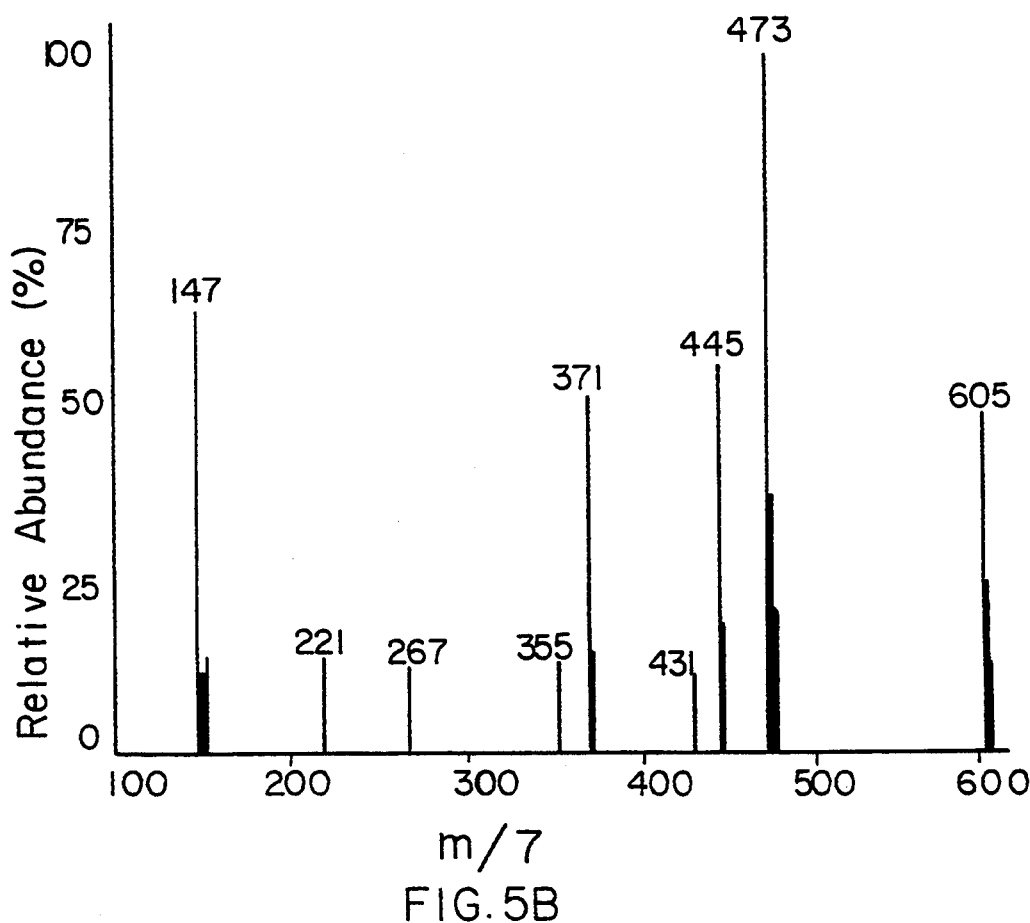
Figure 6A:
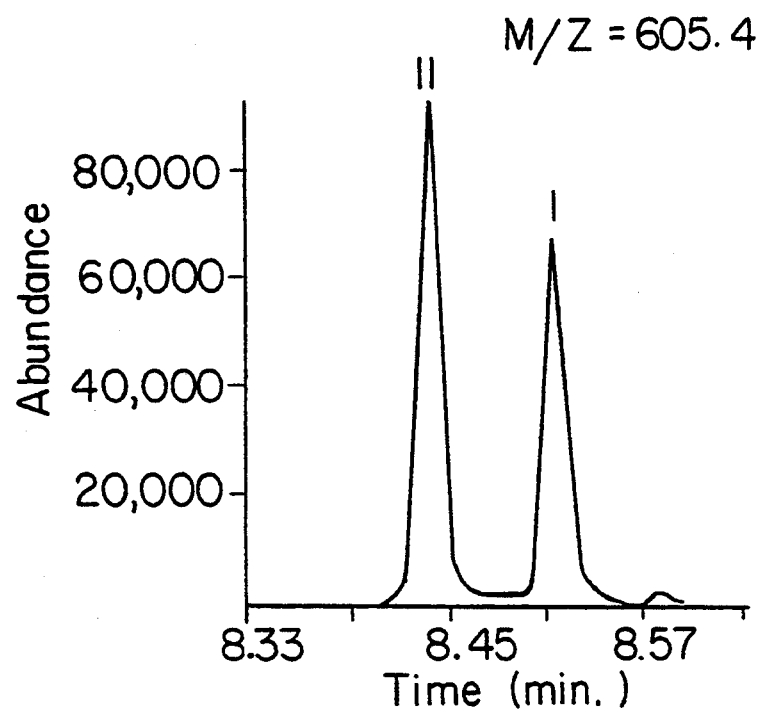
FIG. 6A and 6B illustrates the chromatograms of 2-methylcitric acid.
Figure 6B:
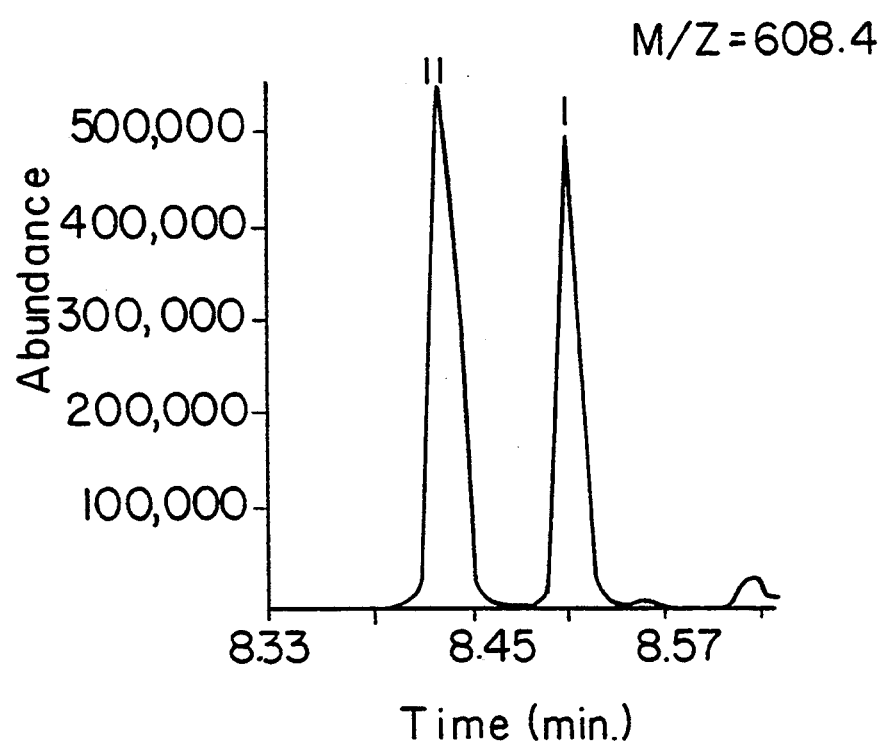

FIG. 5A and 5B show the molecular weights of 2-methylcitric acid and a diagram of the 2-methylcitric acid molecule. Peaks representing the entire molecule, i.e. $[M]^+$ were not observed. FIG. 6A and 6B show the gas chromatogram of 2-methylcitric acid I and II, the top graph being for endogenous 2-methylcitric acid I and II and the bottom graph being for [methyl-$D_3$]2-methylcitric acid I and II.

Although the assay described above is for both 2-methylcitric acid I and 2-methylcitric acid II, it should be appreciated that the assay can actually be used for either compound or both in combination.

Combined Assays

In other experiments of a preferred embodiment of the invention, the second method for assaying cystathionine was combined with the method for assaying 2-methylcitric acid in the following manner: 1) 51 ul of H₂O containing the internal standards for cystathionine, 2-methylcitric acid, homocysteine, and methylmalonic acid was added to 400 ul of serum or cerebral spinal fluid or urine (40 ul urine plus 360 ul of 0.15M NaCl) and 1 ml of H₂O in the initial sequence; 2) 51 ul of H₂O containing 20 mg/ml of dithiothreitol was then added followed by, mixing and a 30 minute incubation at 40° C.; 3) the entire sample was then treated and followed up exactly as described for the 2-methylcitrate assay except that the run-through from the AG MP-1 was saved instead of being discarded; 4) 51 ul of 1N NaOH containing 10 mg/ml of dithiothreitol was added to the run-through followed by mixing and a second 30 minute incubation at 40° C.; and 5) the treated run-through samples from the preceding step were then applied directly to AG MP-1 columns and eluted with 0.04N acetic acid and methanol exactly as described in the second cystathionine method. In this combined assay, two autosampler vials were obtained for each sample, with the first autosampler vial containing endogenous and internal standards for 2-methylcitric acid and methylmalonic acid and the second autosampler vial containing endogenous and internal standards for cystathionine and homocysteine. During the GC/MS analysis, the peaks for endogenous an the internal standard for methylmalonic acid eluted at approximately 5.0 minutes which were well separated and ahead of the corresponding peaks for 2-methylcitric acid which eluted at approximately 8.5 minutes (see above). During the GC/MS analysis, the peaks for endogenous and the internal standard for homocysteine eluted at approximately 3.8 minutes which were well separated and ahead of the corresponding peaks for cystathionine which eluted at approximately 5.7 minutes (see above).

Clinical Results

Figure 7:
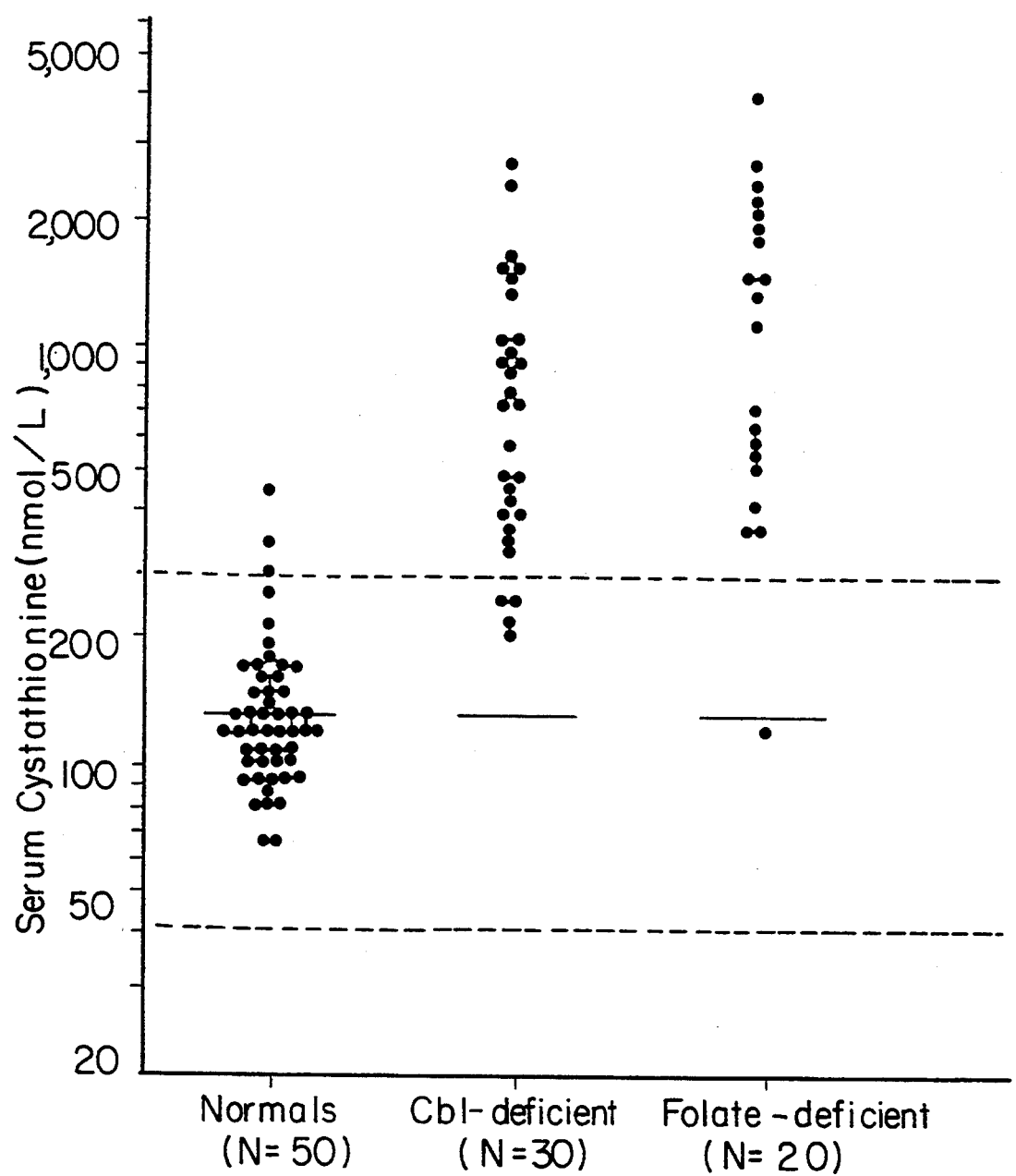
FIG. 7 shows clinical data showing the serum cystathionine levels in nanomoles per liter in normal patients and patients with cobalamin or folic acid deficiency.

FIG. 7 shows on a logarithmic scale the serum cystathionine levels in nanomoles per liter in 50 human patients having no manifestations of any cobalamin or folic acid deficiency, in 30 human patients having a known cobalamin deficiency and in 20 human patients having a known folic acid deficiency. As the Figure suggests, high serum levels of cystathionine generally but not always correspond to either cobalamin or folic acid deficiency.

Table I set forth below shows urine cystathionine levels ("UCYSTAT") from 50 normal subjects in nanomoles per liter.

TABLE I

| | (normal urine cystathionine) | |
|---|---|---|
| | SAMPLE ID | UCYSTAT |
| 1 | NN01 | 7426 |
| 2 | NN02 | 467 |
| 3 | NN03 | 10021 |
| 4 | NN04 | 6077 |
| 5 | NN05 | 3887 |
| 6 | NN06 | 13259 |
| 7 | NN07 | 2343 |
| 8 | NN08 | 2472 |
| 9 | NN09 | 4817 |
| 10 | NN10 | 3736 |
| 11 | NN11 | 8945 |
| 12 | NN12 | 4144 |
| 13 | NN13 | 3515 |
| 14 | NN16 | 38834 |
| 15 | NN17 | 8329 |
| 16 | NN19 | 5723 |
| 17 | NN20 | 20761 |
| 18 | NN21 | 3594 |
| 19 | NN22 | 3603 |

TABLE I-continued

| | (normal urine cystathionine) | |
|---|---|---|
| | SAMPLE ID | UCYSTAT |
| 20 | NN24 | 19063 |
| 21 | NN25 | 4515 |
| 22 | NN26 | 7361 |
| 23 | NN30 | 6665 |
| 24 | NN31 | 680 |
| 25 | NN32 | 2339 |
| 26 | NN33 | 6017 |
| 27 | NN34 | 3592 |
| 28 | NN35 | 547 |
| 29 | NN36 | 21236 |
| 30 | NN37 | 6811 |
| 31 | NN39 | 3245 |
| 32 | NN40 | 3474 |
| 33 | NN41 | 2632 |
| 34 | NN43 | 58 |
| 35 | NN44 | 11953 |
| 36 | NN45 | 691 |
| 37 | NN46 | 5783 |
| 38 | NN47 | 3844 |
| 39 | NN48 | 1875 |
| 40 | NN49 | 3639 |
| 41 | NN50 | 877 |
| 42 | NN52 | 1599 |
| 43 | NN53 | 5318 |
| 44 | NNS4 | 1607 |
| 45 | NN55 | 2079 |
| 46 | NN56 | 936 |
| 47 | NN57 | 10747 |
| 48 | NN58 | 12060 |
| 49 | NN59 | 6175 |
| 50 | NN60 | 1644 |

Table II set forth below shows serum 2-methylcitric acid levels in nanomoles per liter for 50 patients with no cobalamin deficiency. The table is broken into columns for total 2-methylcitric acid ("TOTMC"), the ratio of the two isomers of 2-methylcitric acid ("MCI/MCII"), the second isomer ("MCII") and the first isomer ("MCI").

TABLE II

| | (normal serum 2-methylcitric acid) | | | | |
|---|---|---|---|---|---|
| | SAMPLE ID | TOTMC | MCI/MCII | MCII | MCI |
| 1 | NN55 | 282 | .55 | 181 | 100 |
| 2 | NN03 | 228 | .60 | 143 | 86 |
| 3 | NN46 | 216 | .86 | 117 | 100 |
| 4 | NN11 | 211 | .66 | 127 | 84 |
| 5 | NN06 | 195 | .57 | 124 | 71 |
| 6 | NN18 | 186 | .80 | 104 | 83 |
| 7 | NN58 | 176 | .92 | 92 | 84 |
| 8 | NN49 | 174 | .64 | 106 | 68 |
| 9 | NN25 | 171 | .79 | 96 | 76 |
| 10 | NN50 | 145 | .66 | 87 | 58 |
| 11 | NN26 | 138 | .58 | 87 | 50 |
| 12 | NN43 | 137 | 1.00 | 68 | 68 |
| 13 | NN52 | 136 | .65 | 83 | 54 |
| 14 | NN35 | 136 | 1.09 | 65 | 71 |
| 15 | NN07 | 131 | .59 | 82 | 49 |
| 16 | NN29 | 131 | .59 | 82 | 49 |
| 17 | NN57 | 128 | .56 | 82 | 46 |
| 18 | NN34 | 127 | .75 | 73 | 55 |
| 19 | NN13 | 126 | .79 | 70 | 56 |
| 20 | NN10 | 125 | .58 | 79 | 46 |
| 21 | NN20 | 125 | .56 | 80 | 45 |
| 22 | NN01 | 121 | .55 | 78 | 43 |
| 23 | NN22 | 121 | .57 | 77 | 44 |
| 24 | NN08 | 115 | .64 | 70 | 45 |
| 25 | NN04 | 115 | .77 | 65 | 50 |
| 26 | NN41 | 114 | .52 | 75 | 39 |
| 27 | NN19 | 114 | .61 | 71 | 43 |
| 28 | NN32 | 114 | .58 | 72 | 42 |
| 29 | NN39 | 110 | .52 | 72 | 38 |
| 30 | NN37 | 109 | .75 | 62 | 47 |
| 31 | NN24 | 109 | .60 | 68 | 41 |
| 32 | NN28 | 106 | .66 | 64 | 42 |
| 33 | NN21 | 100 | .88 | 53 | 47 |

TABLE II-continued (normal serum 2-methylcitric acid)

| | SAMPLE ID | TOTMC | MCI/MCII | MCII | MCI |
|---|---|---|---|---|---|
| 34 | NN47 | 100 | .53 | 65 | 35 |
| 35 | NN33 | 94 | .54 | 61 | 33 |
| 36 | NN45 | 93 | .62 | 58 | 36 |
| 37 | NN02 | 93 | .50 | 62 | 31 |
| 38 | NN53 | 92 | .48 | 62 | 30 |
| 39 | NN05 | 92 | .57 | 59 | 33 |
| 40 | NN54 | 91 | .95 | 47 | 45 |
| 41 | NN16 | 91 | .64 | 55 | 35 |
| 42 | NN09 | 87 | .54 | 57 | 31 |
| 43 | NN31 | 83 | .67 | 51 | 31 |
| 44 | NN36 | 80 | .58 | 51 | 29 |
| 45 | NN56 | 79 | .51 | 52 | 26 |
| 46 | NN40 | 78 | .54 | 50 | 27 |
| 47 | NN48 | 70 | .71 | 41 | 29 |
| 48 | NN44 | 69 | .74 | 40 | 29 |
| 49 | NN17 | 66 | .50 | 44 | 22 |
| 50 | NN12 | 66 | .77 | 37 | 28 |

Table III set forth below shows serum 2-methylcitric acid levels for 50 human patients with clinically confirmed cobalamin deficiencies, using the same units and column labels as in Table II.

TABLE III (cobalamin deficient serum 2-methylcitric acid)

| | SAMPLE ID | MCTOT | MCI/MCII | MCII | MCI |
|---|---|---|---|---|---|
| 1 | B7687 | 13509 | .48 | 9121 | 4388 |
| 2 | 12416 | 8826 | .72 | 5146 | 3680 |
| 3 | B4942 | 6028 | .49 | 4050 | 1978 |
| 4 | D3648 | 3296 | .60 | 2057 | 1239 |
| 5 | A3172 | 3071 | .72 | 1787 | 1284 |
| 6 | B2380 | 2965 | .54 | 1924 | 1041 |
| 7 | C8881 | 2757 | .59 | 1732 | 1025 |
| 8 | C9246 | 2728 | .57 | 1739 | 989 |
| 9 | D6354 | 2676 | .59 | 1688 | 988 |
| 10 | D4205 | 2665 | 1.16 | 1232 | 1433 |
| 11 | F1247 | 2594 | .56 | 1663 | 930 |
| 12 | B1330 | 2488 | .62 | 1535 | 953 |
| 13 | 09267 | 2439 | .54 | 1587 | 852 |
| 14 | E1309 | 2251 | .62 | 1385 | 865 |
| 15 | C3384 | 2236 | .64 | 1367 | 869 |
| 16 | F1111 | 2230 | .67 | 1334 | 896 |
| 17 | F7167 | 1892 | .56 | 1215 | 677 |
| 18 | A3511 | 1731 | .68 | 1029 | 702 |
| 19 | C5237 | 1652 | .68 | 986 | 666 |
| 20 | C9834 | 1626 | .65 | 986 | 640 |
| 21 | X1079 | 1619 | .50 | 1079 | 540 |
| 22 | D0883a | 1593 | .58 | 1007 | 587 |
| 23 | D7154 | 1482 | .68 | 883 | 599 |
| 24 | D2459 | 1411 | .67 | 844 | 567 |
| 25 | A8811 | 1345 | .85 | 726 | 618 |
| 26 | E8989 | 1244 | .63 | 762 | 485 |
| 27 | C9199 | 1236 | .98 | 624 | 612 |
| 28 | E9773 | 1068 | .78 | 600 | 468 |
| 29 | D3735 | 875 | .58 | 553 | 322 |
| 30 | F3628 | 791 | .62 | 488 | 303 |
| 31 | F2567 | 774 | .56 | 497 | 276 |
| 32 | F4201 | 697 | .68 | 414 | 283 |
| 33 | D1206 | 637 | .83 | 347 | 289 |
| 34 | D1321a | 604 | .68 | 359 | 245 |
| 35 | C8686a | 581 | .66 | 350 | 231 |
| 36 | D8953 | 483 | .66 | 292 | 191 |
| 37 | A5038 | 447 | .85 | 242 | 206 |
| 38 | C8800 | 398 | .69 | 236 | 162 |
| 39 | F9991 | 393 | .69 | 233 | 160 |
| 40 | D2361 | 370 | .66 | 223 | 148 |
| 41 | D2088 | 326 | .66 | 197 | 130 |
| 42 | C8227 | 300 | .67 | 180 | 120 |
| 43 | E0219 | 297 | .58 | 188 | 109 |
| 44 | 12473 | 266 | .66 | 160 | 106 |
| 45 | D1397a | 224 | .69 | 132 | 92 |
| 46 | D8330 | 214 | .70 | 126 | 88 |
| 47 | D4164 | 206 | .50 | 137 | 69 |
| 48 | C8872 | 203 | .81 | 112 | 91 |
| 49 | A2375 | 202 | .54 | 131 | 71 |

TABLE III-continued (cobalamin deficient serum 2-methylcitric acid)

| | SAMPLE ID | MCTOT | MCI/MCII | MCII | MCI |
|---|---|---|---|---|---|
| 50 | F3977 | 93 | .70 | 55 | 38 |

Table IV set forth below shows serum 2-methylcitric acid levels for 25 human patients with clinically confirmed folic acid deficiencies, using the same units and column labels as in Table II.

TABLE IV (folic acid deficient 2-methylcitric acid)

| | SAMPLE ID | MCTOT | MCI/MCII | MCII | MCI |
|---|---|---|---|---|---|
| 1 | D7348 | 247 | 1.46 | 100 | 147 |
| 2 | A7708 | 238 | .83 | 130 | 108 |
| 3 | B9076 | 234 | .50 | 156 | 78 |
| 4 | B7161 | 230 | .66 | 139 | 92 |
| 5 | B7149 | 210 | .49 | 141 | 69 |
| 6 | A8119 | 209 | .59 | 132 | 77 |
| 7 | E9670 | 189 | .73 | 109 | 80 |
| 8 | C5048 | 171 | .76 | 97 | 74 |
| 9 | 07601 | 166 | .51 | 110 | 56 |
| 10 | E6135 | 130 | .54 | 84 | 46 |
| 11 | 11145 | 125 | .90 | 66 | 59 |
| 12 | C9169 | 123 | 1.07 | 60 | 64 |
| 13 | E4663 | 105 | .58 | 66 | 39 |
| 14 | A7398a | 94 | .50 | 63 | 31 |
| 15 | D0060 | 89 | 1.13 | 42 | 47 |
| 16 | A3285a | 66 | .62 | 41 | 25 |
| 17 | E9405 | 59 | .75 | 34 | 25 |
| 18 | E5653 | 52 | .57 | 33 | 19 |
| 19 | A3769b | 48 | .44 | 33 | 15 |
| 20 | B4551 | 41 | .52 | 27 | 14 |
| 21 | A6199 | 40 | .36 | 29 | 11 |
| 22 | B6301 | 34 | .50 | 22 | 11 |
| 23 | F9010 | 26 | .64 | 16 | 10 |
| 24 | E4492 | 20 | .51 | 13 | 7 |
| 25 | D4162 | 10 | .27 | 8 | 2 |

Figure 8:
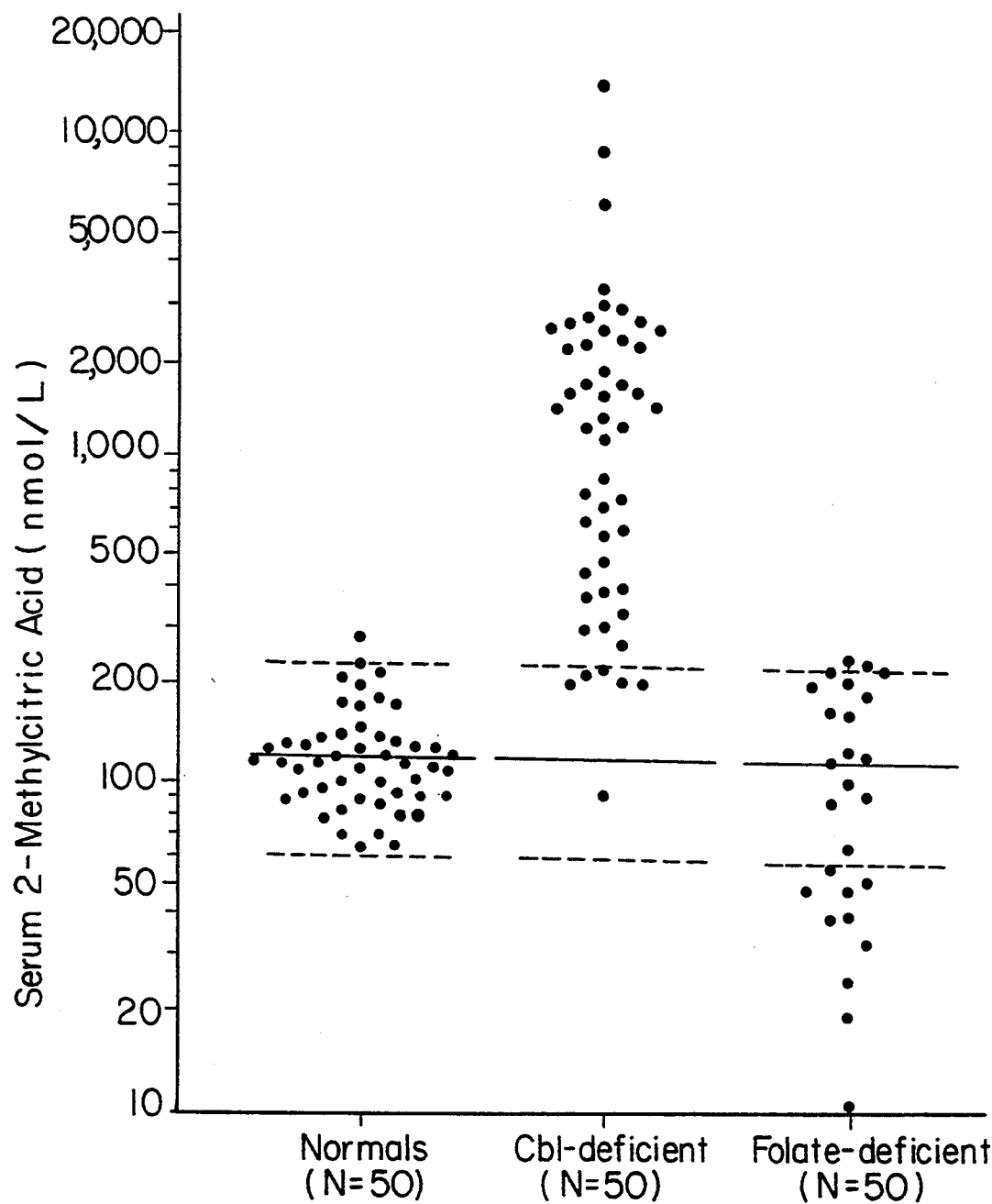
FIG. 8 shows clinical data showing the 2-methylcitric acid levels in nanomoles per liter in normal patients and patients with cobalamin or folic acid deficiencies.

The data tabulated in Tables II–IV is presented in graphic form in FIG. 8 for the two 2-methylcitric acid isomers totalled. As evident from the tables and graph, high levels of 2-methylcitric acid tend to correspond to a cobalamin deficiency but not to a folic acid deficiency.

Table V set forth below shows urine 2-methylcitric acid levels from the same normal subjects as presented in Table II for serum 2-methylcitric acid levels. The table is broken into columns for total urine 2-methylcitric acid ("UMCTOT"), the ratio for the two isomers of urine 2-methylcitric acid ("UMCI/UMCII"), the second isomer ("UMCII") and the first isomer ("UMCI").

TABLE V (normal urine 2-methylcitric acid)

| | SAMPLE ID | UMCTOT | UMCI/UMCII | UMCII | UMCI |
|---|---|---|---|---|---|
| 1 | NN29 | 32296 | .61 | 20101 | 12195 |
| 2 | NN26 | 26298 | .58 | 16631 | 9667 |
| 3 | NN11 | 23574 | .73 | 13608 | 9966 |
| 4 | NN06 | 22666 | .65 | 13724 | 8941 |
| 5 | NN03 | 21617 | .61 | 13429 | 8188 |
| 6 | NN21 | 20501 | .83 | 11229 | 9272 |
| 7 | NN12 | 19289 | .58 | 12225 | 7064 |
| 8 | NN48 | 19239 | .58 | 12187 | 7052 |
| 9 | NN19 | 18999 | .61 | 11797 | 7202 |
| 10 | NN47 | 18651 | .56 | 11962 | 6689 |
| 11 | NN24 | 18279 | .63 | 11220 | 7059 |
| 12 | NN05 | 18141 | .50 | 12075 | 6066 |
| 13 | NN16 | 16259 | .79 | 9491 | 6768 |
| 14 | NN33 | 16227 | .60 | 10143 | 6084 |
| 15 | NN04 | 15363 | .40 | 10996 | 4367 |
| 16 | NN57 | 15238 | .62 | 9402 | 5836 |
| 17 | NN36 | 14761 | .59 | 9293 | 5468 |
| 18 | NN01 | 14463 | .59 | 9098 | 5366 |

TABLE V-continued (normal urine 2-methylcitric acid)

| | SAMPLE ID | UMCTOT | UMCI/UMCII | UMCII | UMCI |
|---|---|---|---|---|---|
| 19 | NN58 | 14243 | .73 | 8223 | 6020 |
| 20 | NN17 | 13851 | .57 | 8840 | 5011 |
| 21 | NN28 | 13492 | .57 | 8611 | 4882 |
| 22 | NN22 | 13395 | .60 | 8346 | 5048 |
| 23 | NN10 | 12630 | .60 | 7914 | 4716 |
| 24 | NN13 | 12339 | .75 | 7044 | 5295 |
| 25 | NN46 | 11740 | .51 | 7755 | 3985 |
| 26 | NN20 | 11527 | .57 | 7328 | 4199 |
| 27 | NN09 | 11094 | .67 | 6647 | 4447 |
| 28 | NN41 | 10893 | .53 | 7140 | 3753 |
| 29 | NN25 | 9883 | .76 | 5620 | 4263 |
| 30 | NN37 | 9330 | .56 | 5995 | 3335 |
| 31 | NN18 | 9200 | .84 | 4999 | 4200 |
| 32 | NN55 | 9165 | .55 | 5908 | 3257 |
| 33 | NN44 | 9162 | .76 | 5203 | 3959 |
| 34 | NN40 | 5910 | .53 | 5807 | 3103 |
| 35 | NN49 | 8246 | .45 | 5687 | 2559 |
| 36 | NN39 | 7733 | .54 | 5014 | 2718 |
| 37 | NN32 | 7358 | .54 | 4778 | 2580 |
| 38 | NN54 | 7159 | .95 | 3672 | 3486 |
| 39 | NN53 | 7145 | .54 | 4643 | 2502 |
| 40 | NN08 | 6265 | .53 | 4100 | 2165 |
| 41 | NN07 | 6008 | .53 | 3935 | 2073 |
| 42 | NN34 | 5570 | .69 | 3303 | 2266 |
| 43 | NN56 | 3492 | .60 | 2180 | 1312 |
| 44 | NN52 | 3416 | .55 | 2204 | 1212 |
| 45 | NN02 | 3062 | .52 | 2018 | 1044 |
| 46 | NN50 | 2535 | .62 | 1564 | 972 |
| 47 | NN35 | 2483 | 1.09 | 1185 | 1297 |
| 48 | NN43 | 1631 | .96 | 834 | 797 |
| 49 | NN45 | 1617 | .51 | 1068 | 549 |
| 50 | NN31 | 859 | .57 | 549 | 310 |

Table VI set forth below shows cerebral spinal fluid 2-methylcitric acid levels for 5 human patients with clinically confirmed cobalamin deficiencies, using the same units and column labels as in Table II. Samples 1-5 are from 5 different human patients, while samples 6 and 7 are from the same human patient as sample 5 during (sample 6) and after (sample 7) cobalamin therapy.

TABLE VI (cobalamin deficient csf 2-methylcitric acid)

| | SAMPLE ID | TOTMC | MCI/MCII | MCII | MCI |
|---|---|---|---|---|---|
| 1 | E9575 | 3742 | 1.71 | 1380 | 2363 |
| 2 | F2217 | 3140 | 3.43 | 709 | 2430 |
| 3 | Z0048 | 16238 | 1.86 | 5681 | 10557 |
| 4 | E9832 | 3967 | 3.49 | 884 | 3084 |
| 5 | F1033 | 5749 | 1.63 | 2184 | 3564 |
| 6 | F1420a | 3660 | 2.13 | 1168 | 2492 |
| 7 | F2124 | 402 | 2.52 | 114 | 287 |

Table VII set forth below shows the declining levels of both serum and urine cystathionine and 2-methylcitric acid levels in a cobalamin deficient human patient that is periodically administered 1000 ug doses of cobalamin over a 13 day period. The cobalamin administrations took place on days 0, 2, 6 and 13

TABLE VII

| | TYPE | SAMPLE ID | TOTMC | MCI/MCII | MCII | MCI |
|---|---|---|---|---|---|---|
| 1 | SERUM | DAY −1 | 1330 | .69 | 786 | 544 |
| 2 | SERUM | DAY 0 | 963 | .69 | 569 | 394 |
| 3 | SERUM | DAY 1 | 819 | .63 | 502 | 317 |
| 4 | SERUM | DAY 2 | 814 | .69 | 481 | 333 |
| 5 | SERUM | DAY 3 | 712 | .69 | 420 | 292 |
| 6 | SERUM | DAY 6 | 347 | .74 | 200 | 147 |
| 7 | SERUM | DAY 13 | 443 | .54 | 287 | 156 |
| 8 | URINE | DAY −1 | 153709 | .74 | 88404 | 65305 |
| 9 | URINE | DAY 0 | 120317 | .72 | 69911 | 50406 |
| 10 | URINE | DAY 1 | 146227 | .69 | 86511 | 59716 |
| 11 | URINE | DAY 2 | 65518 | .71 | 38282 | 27236 |
| 12 | URINE | DAY 3 | 76122 | .71 | 44453 | 31670 |
| 13 | URINE | DAY 6 | 30795 | .73 | 17763 | 13031 |
| 14 | URINE | DAY 13 | 17206 | .59 | 10798 | 6408 |

Table VIII set forth below shows the serum cystathionine and 2-methylcitric acid levels in nanomoles per liter in a cobalamin human patient that was mistakenly treated with oral folic acid at the rate of one mg per day from days 0-11, and then was treated with weekly cobalamin injections of 1000 ug starting on day 35. As the table shows, the folic acid treatments had no significant effect in reducing cystathionine or 2-methylcitric acid levels, but the cobalamin treatment did decrease both cystathionine and 2-methylcitric acid to approximately normal levels.

TABLE VIII

| DAY | CYSTA | MCTOTAL | MCII | MCI |
|---|---|---|---|---|
| 0 | 552 | 1242 | 709 | 533 |
| 23 | 565 | 995 | 529 | 466 |
| 26 | 513 | 1915 | 1128 | 787 |
| 56 | 180 | 211 | 107 | 104 |

From this clinical data, it can be concluded that elevated levels of serum or urine cystathionine levels suggest either a cobalamin deficiency or a folic acid deficiency. Further, elevated levels of serum, urine or cerebral spinal fluid 2-methylcitric acid suggest a cobalamin deficiency but not a folic acid deficiency. Once a cobalamin or folic acid deficiency is detected and distinguished, it can be effectively treated with administrations of the deficient compound. A significant decrease or normalization indicates that the deficiency was due to the vitamin used for treatment. The method described herein for detecting and distinguishing between cobalamin and folic acid deficiencies can be used alone or can be used in combination with or as a backup to other methods such as those that rely on measuring homocysteine or methylmalonic acid.

What is claimed is:

1. A method for detecting a deficiency of cobalamin or folic acid in warm-blooded animals, comprising the steps of:
    assaying a body fluid for an elevated level of cystathionine; and
    correlating an elevated level of cystathionine in said body fluid with a likelihood of a deficiency of cobalamin or folic acid.

2. The method of claim 1, wherein elevated levels of cystathionine indicate a likelihood of a cobalamin or folic acid deficiency.

3. The method of claim 1, wherein said body fluid is one of serum and urine.

4. The method of claim 1, wherein the step of assaying for an elevated level of cystathionine includes:
    combining said body fluid with a compound having cystathionine labelled with an isotope marker;
    measuring the ratio of concentration of the labelled cystathionine and body fluid cystathionine present with a mass spectrometer; and
    determining the concentration of body fluid cystathionine present in said body fluid.

5. The method of claim 4, wherein said step of assaying for an elevated level of cystathionine includes derivatizing the cystathionine before measuring the ratio of concentration of the labelled cystathionine and body fluid cystathionine.

6. The method of claim 5, wherein said derivatization is accomplished by exposing the cystathionine to N-methyl-N(tert-butyl dimethylsylyl) trifluoroacetamide.

7. The method of claim 4, wherein said compound includes deuterated cystathionine.

8. A method of diagnosing and treating a deficiency of cobalamin in a human patient, comprising detecting a cobalamin deficiency in accordance with the steps of claim 1, and administering cobalamin to the human patient in an amount sufficient to return the cystathionine levels to normal.

9. A method of for detecting a deficiency of cobalamin in warm-blooded animals, comprising the steps of:
assaying a body fluid for an elevated level of 2-methylcitric acid I or 2-methylcitric acid II or both; and
correlating an elevated level of 2-methylcitric acid I or 2-methylcitric acid II or both in said body fluid with a likelihood of a deficiency of cobalamin.

10. The method of claim 9, wherein elevated levels of 2-methylcitric acid I or 2-methylcitric acid II or both indicate a likelihood of a cobalamin deficiency.

11. The method of claim 9, wherein said body fluid is serum, urine or cerebral spinal fluid.

12. The method of claim 11, wherein said body fluid is cerebral spinal fluid.

13. The method of claim 9, wherein the step of assaying for an elevated level of 2-methylcitric acid I or 2-methylcitric acid II or both includes:
combining said body fluid with a compound having 2-methylcitric acid I labelled with an isotope marker or a compound having 2-methylcitric acid II labelled with an isotope marker or both;
measuring the ratio of concentration of the labelled 2-methylcitric acid I or 2-methylcitric acid II or both and body fluid 2-methylcitric acid I or 2-methylcitric acid II or both with a mass spectrometer; and
determining the concentration of body fluid 2-methylcitric acid I or 2-methylcitric acid II or both in said body fluid.

14. The method of claim 13, wherein said step of assaying for an elevated level of 2-methylcitric acid I or 2-methylcitric acid II or both includes derivatizing the 2-methylcitric acid I or 2-methylcitric acid II or both before measuring the ratio of concentration of the labelled 2-methylcitric acid I or 2-methylcitric acid II or both and body fluid 2-methylcitric acid I or 2-methylcitric acid II or both.

15. The method of claim 14, wherein said derivatization is accomplished by exposing the 2-methylcitric acid I or 2-methylcitric acid II or both to N-methyl-N(tert-butyl dimethylsylyl) trifluoroacetamide.

16. The method of claim 13, wherein said compound includes deuterated 2-methylcitric acid I or 2-methylcitric acid II or both.

17. A method of diagnosing and treating a deficiency of cobalamin in a human patient, comprising detecting a cobalamin deficiency in accordance with the steps of claim 9, and administering cobalamin to the human patient in an amount sufficient to return the levels of 2-methylcitric acid I or 2-methylcitric acid II or both to normal.

18. A method for detecting a deficiency of cobalamin or folic acid in warm-blooded animals and for distinguishing between a deficiency of cobalamin and a deficiency of folic acid, comprising the steps of:
assaying a first body fluid from said warm-blooded animal for an elevated level of cystathionine;
correlating an elevated level of cystathionine in said body fluid with a likelihood of a deficiency of cobalamin or folic acid;
assaying a second body fluid from said warm-blooded animal having an elevated level of cystathionine in said first body fluid correlating with a likelihood of a deficiency of cobalamin or folic acid, for an elevated level of 2-methylcitric acid I or 2-methylcitric acid II or both; and
correlating an elevated level of 2-methylcitric acid I or 2-methylcitric acid II or both in said second body fluid with a likelihood of a deficiency of cobalamin but both a likelihood of a deficiency of folic acid.

19. The method of claim 18, wherein elevated levels of cystathionine indicate a likelihood of a cobalamin of folic acid deficiency, and elevated levels of 2-methylcitric acid I or 2-methylcitric acid II or both indicate a likelihood of a cobalamin deficiency but not a likelihood of a folic acid deficiency.

20. The method of claim 19, wherein said first body fluid is serum or urine, and said second body fluid is serum, urine or cerebral spinal fluid.

21. The method of claim 20, wherein said first and second body fluids are the same.

22. The method of claim 18:
wherein the step of assaying for an elevated level of cystathionine includes combining said first body fluid with a first compound having cystathionine labelled with an isotope marker, and the step of assaying for an elevated level of 2- methylcitric acid I or 2-methylcitric acid II or both includes combining said second body fluid with a second compound having 2-methylcitric acid I or 2-methylcitric acid II or both labelled with an isotope marker; and
further comprising measuring the ratio of concentration of the labelled cystathionine and body fluid cystathionine and the ratio of concentration of the labelled 2-methylcitric acid I or 2-methylcitric acid II or both and body fluid 2-methylcitric acid I or 2-methylcitric acid II or both; and determining the concentration of body fluid cystathionine present in said first body fluid and determining the concentration of body fluid 2-methylcitric acid I or 2-methylcitric acid II or both in said second body fluid.

23. The method of claim 22, wherein said first and second body fluids are the same, and wherein the first compound having a known amount of labelled cystathionine and the second compound having a known amount of labelled 2-methylcitric acid I or 2-methylcitric acid II or both are added to a single sample or said body fluid, and wherein the single sample is divided into a first sample for measuring cystathionine and a second sample for measuring 2-methylcitric acid I or 2-methylcitric acid II or both.

24. The method of claim 22, wherein said steps of assaying for an elevated level of cystathionine and 2-methylcitric acid I or 2-methylcitric acid II or both includes derivatizing the cystathionine and 2-methylcitric acid I or 2-methylcitric acid II or both before measuring the ratio of concentration of the labelled cystathionine and body fluid cystathionine and the ratio of concentration of the labelled 2-methylcitric acid I or 2-methylcitric acid II or both and body fluid 2-methylcitric acid I or 2-methylcitric acid II or both.

25. The method of claim 24, wherein said derivatization is accomplished by exposing the cystathionine and 2-methylcitric acid I or 2-methylcitric acid II or both to N-methyl-N(tert-butyl dimethylsylyl)trifluoroacetamide.

26. The method of claim 22, wherein said first compound includes deuterated cystathionine and said second compound includes deuterated 2-methylcitric acid I of 2-methylcitric acid II or both.

27. The method of diagnosing and treating a deficiency of cobalamin in a human patient, comprising for detecting cobalamin deficiency in accordance with the steps of claim 18, and administering cobalamin to the human patient in an amount sufficient to return to normal the elevated level of cystathionine, or 2-methylcitric acid I or 2-methylcitric acid II or both.

28. A method of diagnosing and treating a deficiency of folic acid in a human patient, comprising detecting folic acid deficiency in accordance with the steps of claim 18, and administering folic acid to the human patient in an amount sufficient to return to normal the elevated level of cystathionine.

29. A method for detecting a deficiency of cobalamin or folic acid in warm-blooded animals, comprising the steps of:
  assaying a first body fluid for an elevated level of cystathionine;
  assaying a second body fluid for an elevated level of homocysteine; and
  correlating an elevated level of cystathionine and homocysteine with a likelihood of a deficiency of cobalamin or folic acid.

30. The method of claim 29, wherein said first and second body fluids are serum or urine.

31. The method of claim 30, wherein said first and second body fluids are the same.

32. The method of claim 31, wherein said steps of assaying the body fluid for an elevated level of cystathionine and assaying said body fluid for an elevated level of homocysteine includes:
  combining the body fluid with a first compound having a cystathionine labelled with an isotope marker and with a second compound having homocysteine labelled with an isotope marker;
  measuring the ratio of concentration of the labelled cystathionine and body fluid cystathionine and the ratio of concentration of the labelled homocysteine and body fluid homocysteine with a mass spectrometer; and
  determining the concentration of body fluid cystathionine and homocysteine present in said body fluid.

33. The method of claim 32, wherein the first compound and second compound are added to a single sample of said body fluid.

34. The method of claim 32, wherein said step of assaying for elevated levels of cystathionine and homocysteine includes derivatizing each of the cystathionine and homocysteine before measuring the ratio of concentration of each of the cystathionine and homocysteine and body fluid cystathionine and homocysteine.

35. The method of claim 34, wherein said derivatization is accomplished by exposing the cystathionine and homocysteine to N-methyl-N(tert-butyl dimethylsylyl)-trifluoroacetamide.

36. The method of claim 32, wherein said first compound includes deuterated cystathionine and said second compound includes deuterated homocysteine.

37. The method of claim 28, further comprising the following steps for distinguishing between a likelihood of cobalamin deficiency and a likelihood of a folic acid deficiency:
  assaying a third body fluid for an elevated level of at least one substance chosen from methylmalonic acid, 2-methylcitric acid I or 2-methylcitric acid II or both; and
  correlating an elevated level of said chosen substance methylmalonic acid or 2-methylcitric acid I or 2-methylcitric acid II or both with a likelihood of a deficiency or cobalamin but not a likelihood of a deficiency of folic acid.

38. The method of claim 37, wherein the third body fluid is assayed for 2-methylcitric acid I or 2-methylcitric acid II or both and said body fluids are serum, urine or cerebral spinal fluid.

39. The method of claim 38, wherein said first, second and third body fluids are the same.

40. The method of claim 37, wherein the third body fluid is assayed for an elevated level of 2-methylcitric acid I or 2-methylcitric acid II or both in accordance with the steps of:
  combining said third body fluid with a compound having 2-methylcitric acid I labelled with an isotope marker or 2-methylcitric acid II labelled with an isotope marker or both; measuring the ratio of concentration of labelled 2-methylcitric acid I or 2-methylcitric acid II or both and body fluid 2-methylcitric acid I or 2-methylcitric acid II or both with a mass spectrometer; and determining the concentration of body fluid 2-methylcitric acid I or 2-methylcitric acid II or both in said body fluid.

41. The method of claim 40, wherein said first, second and third body fluids are the same, and a first compound having labelled cystathionine, a second compound having labelled homocysteine and a third compound having labelled 2-methylcitric acid I or 2-methylcitric acid II or both are added to a single sample of said body fluid, and the single sample is divided into a first sample for measuring cystathionine and homocysteine and a second sample for measuring 2-methylcitric acid I or 2-methylcitric acid II or both.

42. The method of claim 37, wherein the third body fluid is assayed for 2-methylcitric acid I or 2-methylcitric acid II or both and said assay includes derivatizing the 2-methylcitric acid I or 2-methylcitric acid II or both before measuring the ratio of concentration of labelled 2-methylcitric acid I or 2-methylcitric acid II or both and body fluid 2-methylcitric acid I or 2-methylcitric acid II or both.

43. The method of claim 42, wherein said derivatization is accomplished by exposing the 2-methylcitric acid to N-methyl-N(tert-butyl dimethylsylyl) trifluoroacetamide.

44. The method of claim 40, wherein said third compound includes deuterated 2-methylcitric acid I or 2-methylcitric acid II or both.

45. A method for detecting a deficiency of cobalamin in warm-blooded animals, comprising the steps of:
  assaying a first body fluid for elevated level of 2-methylcitric acid I or 2-methylcitric acid II or both;
  assaying a second body fluid for an elevated level of methylmalonic acid; and correlating an elevated level of 2-methylcitric acid I or 2-methylcitric acid II or both and methylmalonic acid with a likelihood of a deficiency of cobalamin.

46. The method of claim 45, wherein said first and second body fluids are serum, urine or cerebral spinal fluid.

47. The method of claim 46, wherein said first and second body fluids are the same.

48. The method of claim 45, wherein said step of assaying a first body fluid for an elevated level of 2-methylcitric acid I or 2-methylcitric acid II or both is in accordance with the steps of:
combining said third body fluid with a compound having 2-methylcitric acid I labelled with an isotope marker or 2-methylcitric acid II labelled with an isotope marker or both; measuring the ratio of concentration of labelled 2-methylcitric acid I or 2-methylcitric acid II or both and body fluid 2-methylcitric acid I or 2-methylcitric acid II or both with a mass spectrometer; and determining the concentration of body fluid 2-methylcitric acid I or 2-methylcitric acid II or both in said body fluid.

49. The method of claim 48, wherein said step of assaying a for an elevated level of 2-methylcitric acid I or 2-methylcitric acid II or both includes derivatizing the 2-methylcitric acid I or 2-methylcitric acid II or both before measuring the ratio of concentration of labelled 2-methylcitric acid I or 2-methylcitric acid II or both and the body fluid 2-methylcitric acid I or 2-methylcitric acid II or both.

50. The method of claim 49, wherein said derivatization is accomplished by exposing the 2-methylcitric acid I or 2-methylcitric acid II or both to N-methyl-N(tert-butyl dimethylsylyl) trifluoroacetamide.

51. The method of claim 48, wherein 2-methylcitric acid I or 2-methylcitric acid II or both includes deuterated 2-methylcitric acid I or 2-methylcitric acid II or both.

52. A method for detecting a deficiency of cobalamin or folic acid in warm-blooded animals, and for distinguishing between a deficiency of cobalamin and a deficiency of folic acid, comprising the steps of:
assaying a first body fluid for an elevated level of one of cystathionine and homocysteine;
correlating elevated levels of cystathionine and homocysteine with a likelihood of a deficiency of cobalamin or folic acid;
assaying a second body fluid for an elevated level of methylmalonic acid;
assaying a third body fluid for an elevated level of 2-methylcitric acid I or 2-methylcitric acid II or both; and
correlating elevated levels of methylmalonic acid and 2-methylcitric acid I or 2-methylcitric acid II or both with a likelihood of a deficiency of cobalamin but not a likelihood of a deficiency of folic acid.

53. The method of claim 52, wherein said first body fluid is serum or urine and said second and third body fluids are serum, urine or cerebral spinal fluid.

54. The method of claim 53, wherein said first, second and third body fluids are the same.

55. The method of claim 52, wherein said steps of assaying the first body fluid for an elevated level of one of cystathionine and homocysteine includes:
combining said first body fluid with a compound having one of cystathionine and homocysteine labelled with an isotope marker;
measuring the ratio of concentration of one of labelled cystathionine and body fluid cystathionine with a mass spectrometer; and
determining the concentration of body fluid cystathionine or homocysteine present in said body fluid.

56. The method of claim 55, wherein said step of assaying said third body fluid for an elevated level of 2-methylcitric acid I or 2-methylcitric acid II or both includes the steps of:
combining said third body fluid with a compound having 2-methylcitric acid I labelled with an isotope marker or 2-methylcitric acid II labelled with an isotope marker or both; measuring the ratio of concentration of labelled 2-methylcitric acid I or 2-methylcitric acid II or both and body fluid 2-methylcitric acid I or 2-methylcitric acid II or both with a mass spectrometer; and determining the concentration of body fluid 2-methylcitric acid I or 2-methylcitric acid II or both in said body fluid.

57. The method of claim 56, wherein said first, second and third body fluids are the same, and a first compound having one of cystathionine and homocysteine, a second compound having labelled methylmalonic acid, and a third compound having labelled 2-methylcitric acid I or 2-methylcitric acid II or both are added to a single sample of said body fluid, and the single sample is divided into a first sample for measuring said one of cystathionine and homocysteine and a second sample for measuring methylmalonic acid and 2-methylcitric acid I or 2-methylcitric acid II or both.

58. The method of claim 56, wherein said steps of assaying includes derivatizing the assayed compound before measuring the ratio of concentration of labelled compound and the body fluid compound.

59. The method of claim 58, wherein said derivatization is accomplished by exposing the assayed compound to N-methyl-N(tert-butyl dimethylsylyl) trifluoroacetamide.

60. The method of claim 54, wherein said compound includes deuterated forms of the assayed compound.

61. A method for detecting a deficiency of cobalamin or folic acid in a warm-blooded animal and for distinguishing between a deficiency of cobalamin and a deficiency of folic acid, comprising the steps of:
assaying a first body fluid for an elevated level of cystathionine;
assaying a second body fluid for an elevated level of homocysteine;
correlating said elevated levels of cystathionine and homocysteine with a likelihood of a deficiency of cobalamin or folic acid;
assaying a third body fluid for an elevated level of methylmalonic acid;
assaying a fourth body fluid for an elevated level of 2-methylcitric acid I or 2-methylcitric acid II or both; and
correlating said elevated levels of methylmalonic acid and 2-methylcitric acid I or 2-methylcitric acid II or both with a likelihood of a deficiency of cobalamin but not a likelihood of a deficiency of folic acid.

62. The method of claim 60, wherein said body fluids are serum, urine or cerebral spinal fluid.

63. The method of claim 62, wherein said body fluids are the same.

64. The method of claim 61, wherein said step of assaying the first body fluid for an elevated level of cystathionine includes the steps of:

combining said first body fluid with a compound having cystathionine labelled with an isotope marker; measuring the ratio of concentration of labelled cystathionine and first body fluid cystathionine with a mass spectrometer; and determining the concentration of first body fluid cystathionine present in said first body fluid.

65. The method of claim 64, wherein said first, second, third and fourth body fluids are the same, and a first compound having labelled cystathionine, a second compound having labelled homocysteine, a third compound having labelled methylmalonic acid, and a fourth compound having labelled 2-methylcitric acid I or 2-methylcitric acid II or both, are added to a single sample of said body fluid, and the single sample is divided into a first sample for measuring homocysteine and cystathionine and a second sample for measuring methylmalonic acid and 2-methylcitric acid I or 2-methylcitric acid II or both.

66. The method of claim 64, wherein said step of assaying the fourth body fluid for an elevated level of 2-methylcitric acid I or 2-methylcitric acid II or both includes the steps of:
 derivatizing the 2-methylcitric acid I or 2-methylcitric acid II or both before measuring the ratio of concentration of the labelled 2-methylcitric acid I or 2-methylcitric acid II or both and body fluid 2-methylcitric acid I or 2-methylcitric acid II or both.

67. The method of claim 66, wherein said steps of assaying include derivatizing the assayed compound before measuring the ratio of concentration of labelled compound and body fluid compound.

68. The method of claim 67, wherein said derivatization is accomplished by exposing the assayed compound to N-methyl-N(tert-butyl dimethylsylyl) trifluoroacetamide.

69. The method of claim 67, wherein said compounds include deuterated forms of the assayed compound.

* * * * *

UNITED STATES PATENT AND TRADEMARK OFFICE
CERTIFICATE OF CORRECTION

PATENT NO. : 5,374,560
DATED : December 20, 1994
INVENTOR(S) : Robert H. Allen, Sally P. Stabler and John Lindenbaum It is certified that error appears in the above—identified patent and that said Letters Patent is hereby corrected as shown below:

Column 2, Line 57, change "$\leq$" to --$\leq$--

Column 6, Line 37, change "1989" to --1981--

Column 8, Lines 47 and 48, add <u>at 40°C for 30 minutes, 51 Ul of H$_2$O containing 83 mg/ml</u> after the word "incubation" and before the word "of"

Column 9, Line 33, add the words <u>it is</u> after the word "for" and before the word "added"

Column 10, Line 27, add <u>8.5</u> before the word "minutes" and after the word "approximately"

Column 11, Line 25, change "an" to --and--

Column 18, Line 57, change "or" to --of--

Signed and Sealed this

Twenty-fourth Day of October, 1995

Attest:

BRUCE LEHMAN

Attesting Officer    Commissioner of Patents and Trademarks